(12) United States Patent
Hendrix et al.

(10) Patent No.: US 11,730,555 B2
(45) Date of Patent: Aug. 22, 2023

(54) SURGICAL DRAPE FOR THERMAL TREATMENT BASIN

(71) Applicant: Microtek Medical, Inc., Columbus, MS (US)

(72) Inventors: Heidi Frances Hendrix, Brookhaven, GA (US); David Richard Rawlings, Cumming, GA (US); Michelle Wilson, Caledonia, MS (US)

(73) Assignee: Microtek Medical, Inc., Columbus, MS (US)

( * ) Notice: Subject to any disclaimer, the term of this patent is extended or adjusted under 35 U.S.C. 154(b) by 866 days.

(21) Appl. No.: 16/144,706

(22) Filed: Sep. 27, 2018

(65) Prior Publication Data
US 2019/0090972 A1 Mar. 28, 2019

Related U.S. Application Data

(60) Provisional application No. 62/564,229, filed on Sep. 27, 2017.

(51) Int. Cl.
*A61B 46/00* (2016.01)
*A61B 46/10* (2016.01)
(Continued)

(52) U.S. Cl.
CPC .............. *A61B 46/10* (2016.02); *A61B 46/40* (2016.02); *A61F 7/0085* (2013.01); *A61F 7/0241* (2013.01)

(58) Field of Classification Search
CPC .. B65D 1/34; B65D 1/36; A61B 50/37; A61B 50/36; A61B 50/33; A61B 50/34;
(Continued)

(56) References Cited

U.S. PATENT DOCUMENTS 3,770,119 A * 11/1973 Hultberg ................ A61B 50/30
206/439
3,777,749 A 12/1973 Collins
(Continued)

FOREIGN PATENT DOCUMENTS

AU 2016200812 B2 11/2016
CA 2620906 A1 3/2006
(Continued)

OTHER PUBLICATIONS

International Patent Application No. PCT/US2018/053154, Invitation to Pay Additional Fees and Partial Search Report dated Jan. 2, 2019, 16 pages.
(Continued)

*Primary Examiner* — Adam Baker
(74) *Attorney, Agent, or Firm* — Fredrikson & Byron, P.A.

(57) ABSTRACT

A drape for a piece of equipment used during a medical procedure may be formed of a flexible sheet of polymeric material. The flexible sheet can have a basin portion shape-indexed to a basin or reservoir of the piece of equipment over which the drape is intended to be draped. The flexible sheet can also have a side sheet portion connected to the basin portion. The side sheet portion can drape down the basin or reservoir of the piece of equipment over which the drape is draped. The basin portion of the flexible sheet can be collapsible. As a result, the drape can be collapsed into planar package for storage. Upon being removed from the package, the basin portion of the drape can be expanded to conform to the walls of the basin of the piece of equipment over which the drape is deployed.

13 Claims, 21 Drawing Sheets

(51) Int. Cl.
*A61F 7/00* (2006.01)
*A61F 7/02* (2006.01)

(58) Field of Classification Search
CPC ......... A61B 50/30; A61B 50/20; A61B 50/15;
A61B 50/24; A61B 46/10; A61B 46/23;
A61B 46/40; A61B 2046/236; A47G
2021/002
USPC ........................................................ 128/849
See application file for complete search history.

(56) References Cited

U.S. PATENT DOCUMENTS

| | | | |
|---|---|---|---|
| 4,042,109 A * | 8/1977 | Barcan | A61F 15/001 |
| | | | 206/440 |
| 4,889,231 A * | 12/1989 | Foote | B65D 1/34 |
| | | | 206/363 |
| 4,934,152 A | 6/1990 | Templeton | |
| 4,944,427 A * | 7/1990 | Yamada | A61B 50/33 |
| | | | 220/495.01 |
| 5,163,299 A | 11/1992 | Faries, Jr. et al. | |
| 5,331,820 A | 7/1994 | Faries, Jr. et al. | |
| 5,333,326 A | 8/1994 | Faries, Jr. et al. | |
| 5,400,616 A | 3/1995 | Faries, Jr. et al. | |
| 5,402,644 A | 4/1995 | Faries, Jr. et al. | |
| 5,429,801 A | 7/1995 | Faries, Jr. et al. | |
| 5,435,322 A * | 7/1995 | Marshall | A61B 46/10 |
| | | | 128/849 |
| 5,443,082 A | 8/1995 | Mewburn | |
| 5,457,962 A | 10/1995 | Faries, Jr. et al. | |
| 5,502,980 A | 4/1996 | Faries, Jr. et al. | |
| 5,522,095 A | 6/1996 | Faries, Jr. et al. | |
| 5,524,643 A | 6/1996 | Faries, Jr. et al. | |
| 5,551,240 A | 9/1996 | Faries, Jr. et al. | |
| 5,615,423 A | 4/1997 | Faries, Jr. et al. | |
| 5,653,938 A | 8/1997 | Faries, Jr. et al. | |
| 5,809,788 A | 9/1998 | Faries, Jr. et al. | |
| 5,816,252 A | 10/1998 | Faries, Jr. et al. | |
| 5,857,467 A | 1/1999 | Faries, Jr. et al. | |
| 5,879,621 A | 3/1999 | Faries, Jr. et al. | |
| 5,950,438 A | 9/1999 | Faries, Jr. et al. | |
| 5,964,161 A * | 10/1999 | Conway | B60N 3/002 |
| | | | 108/43 |
| 6,003,328 A | 12/1999 | Faries, Jr. et al. | |
| 6,035,855 A | 3/2000 | Faries, Jr. et al. | |
| 6,087,636 A | 7/2000 | Faries, Jr. et al. | |
| 6,091,058 A | 7/2000 | Faries, Jr. et al. | |
| 6,255,627 B1 | 7/2001 | Faries, Jr. et al. | |
| 6,371,121 B1 | 4/2002 | Faries, Jr. et al. | |
| 6,615,836 B1 | 9/2003 | Griesbach et al. | |
| 6,810,881 B2 | 11/2004 | Faries, Jr. et al. | |
| 6,860,271 B2 | 3/2005 | Faries, Jr. | |
| 6,910,485 B2 | 6/2005 | Faries, Jr. et al. | |
| 6,918,395 B2 | 7/2005 | Faries, Jr. et al. | |
| 7,128,275 B2 | 10/2006 | Kammer et al. | |
| 7,176,030 B2 | 2/2007 | Faries, Jr. et al. | |
| D546,943 S | 7/2007 | Kammer et al. | |
| D546,944 S | 7/2007 | Kammer et al. | |
| D547,444 S | 7/2007 | Kammer et al. | |
| 7,347,210 B2 | 3/2008 | Faries, Jr. et al. | |
| 7,350,373 B1 | 4/2008 | Faries, Jr. et al. | |
| D568,989 S | 5/2008 | Kammer et al. | |
| D569,970 S | 5/2008 | Kammer et al. | |
| 7,398,738 B2 | 7/2008 | Newhouse et al. | |
| 7,418,966 B2 | 9/2008 | Faries, Jr. et al. | |
| 7,441,714 B2 | 10/2008 | Kammer et al. | |
| 7,459,657 B2 | 12/2008 | Kammer et al. | |
| 7,560,667 B2 | 7/2009 | Kammer et al. | |
| 7,654,402 B2 * | 2/2010 | Kusuma | B65D 21/086 |
| | | | 220/666 |
| 7,671,302 B1 | 3/2010 | Faries, Jr. et al. | |
| 7,728,262 B1 | 6/2010 | Faries, Jr. et al. | |
| 7,854,387 B2 | 12/2010 | Kammer et al. | |
| 7,903,957 B2 | 3/2011 | Kammer et al. | |
| 7,959,860 B2 | 6/2011 | Faries, Jr. et al. | |
| 8,138,454 B2 | 3/2012 | Kammer et al. | |
| 8,148,667 B2 | 4/2012 | Faries, Jr. et al. | |
| 8,925,125 B2 | 1/2015 | Galinier | |
| 9,367,061 B2 | 6/2016 | Miller et al. | |
| 2004/0045954 A1 * | 3/2004 | Lehman | A61L 2/26 |
| | | | 219/521 |
| 2004/0208780 A1 * | 10/2004 | Faries, Jr. | A61B 46/10 |
| | | | 422/3 |
| 2008/0017292 A1 | 1/2008 | Gammons et al. | |
| 2008/0065264 A1 | 3/2008 | Omura et al. | |
| 2008/0152937 A1 | 6/2008 | Kammer et al. | |
| 2008/0264967 A1 | 10/2008 | Schifman et al. | |
| 2009/0112057 A1 | 4/2009 | Kammer et al. | |
| 2009/0113618 A1 | 5/2009 | Slayton | |
| 2009/0198347 A1 | 8/2009 | Kirzinger | |
| 2009/0255540 A1 | 10/2009 | Faries, Jr. | |
| 2013/0152946 A1 | 6/2013 | Sosnowski | |
| 2013/0247921 A1 * | 9/2013 | Dye | A61B 46/00 |
| | | | 128/853 |
| 2013/0293353 A1 * | 11/2013 | McPherson | G06K 19/07798 |
| | | | 340/10.1 |
| 2014/0041669 A1 * | 2/2014 | Houde | A61B 50/13 |
| | | | 128/849 |
| 2014/0208986 A1 | 7/2014 | Desroches et al. | |
| 2017/0274136 A1 | 9/2017 | Hendrix et al. | |
| 2017/0274157 A1 | 9/2017 | Hendrix et al. | |

FOREIGN PATENT DOCUMENTS

| | | | |
|---|---|---|---|
| CA | 2620907 | A1 | 3/2006 |
| CN | 201384756 | Y | 1/2010 |
| CN | 202885227 | U | 4/2013 |
| CN | 204033502 | U | 12/2014 |
| CN | 106473635 | A | 3/2017 |
| EP | 401591 | A2 | 3/1993 |
| JP | H0698852 | A | 4/1994 |
| JP | 2004333048 | A | 11/2004 |
| JP | 2016502435 | A | 1/2016 |
| RU | 2219950 | C2 | 12/2003 |
| RU | 2352312 | C2 | 4/2009 |
| RU | 2428138 | C2 | 9/2011 |
| RU | 2493796 | C2 | 9/2013 |

OTHER PUBLICATIONS

International Patent Application No. PCT/US2018/053154, International Search Report and Written Opinion dated Feb. 27, 2019, 21 pages.

* cited by examiner

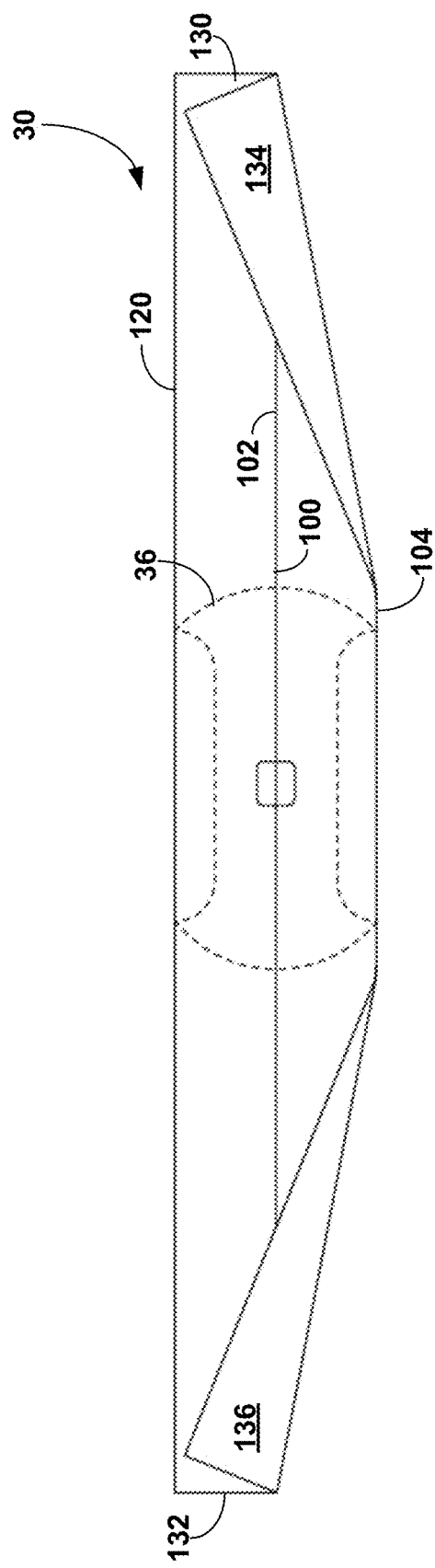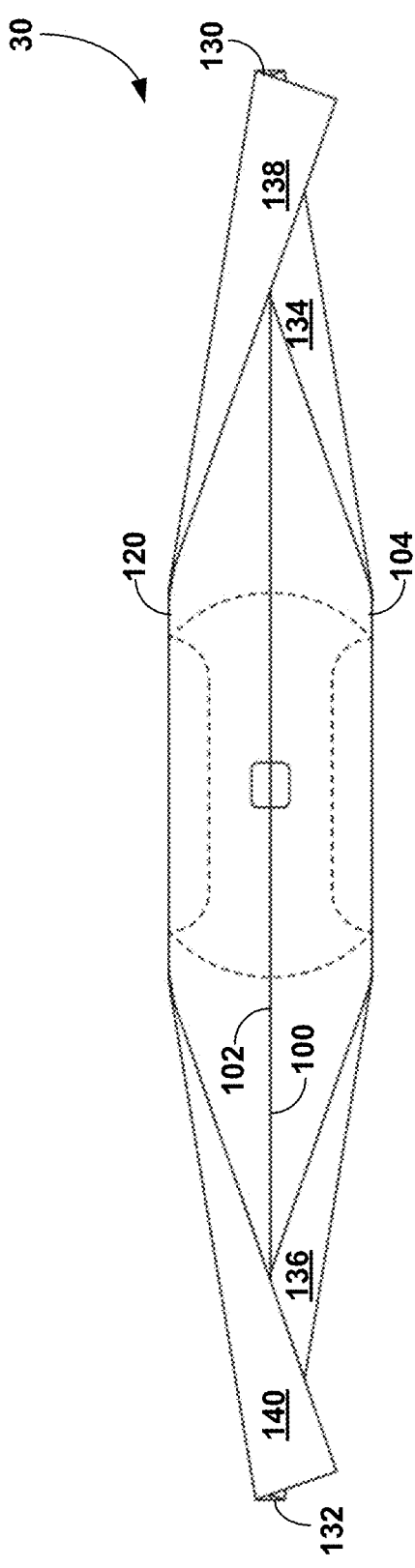
FIG. 20
FIG. 21

SURGICAL DRAPE FOR THERMAL TREATMENT BASIN

CROSS-REFERENCE

This application claims priority to U.S. Provisional Patent Application No. 62/564,229, filed Sep. 27, 2017, the entire contents of which are incorporated herein by reference.

TECHNICAL FIELD

This disclosure relates to surgical drapes and, more particularly, surgical drapes used to cover medical equipment during a procedure.

BACKGROUND

Disposable surgical drapes are used to help establish or maintain a sterile field during a medical procedure, reducing the likelihood that a patient undergoing the procedure will be infected from contaminated surfaces or objects. For example, a sterile surgical drape may be deployed over a piece of equipment used in the surgical suite or other medical environment prior to the start of the procedure. The sterile surgical drape can provide a barrier between materials introduced into and/or removed from the patient during the procedure and the equipment being used during the procedure. Even though the equipment itself may be sterilized before use, the addition of a sterile surgical drape can reduce the likelihood of patient contamination and hospital-acquired infection during the procedure.

In practice, a sterile surgical drape may be provided as a pre-packaged, disposable item. The sterile surgical drape may be packed sufficiently small so as to be conveniently transported and stored. However, the sterile surgical drape may have an unpackaged size adequate to cover the intended medical equipment. To help avoid contact contamination during deployment of the sterile surgical drape, the drape may be folded and packaged so as to minimize contact of sterile surfaces by a user deploying the drape.

SUMMARY

In general, this disclosure is directed to surgical drapes as well as techniques for folding surgical drapes for convenient packaging and unfolding surgical drapes for sterile deployment. In some examples, a surgical drape is designed to cover a basin of a surgical system, such as a system for thermally treating surgical fluid before utilizing the fluid during a medical procedure. The surgical fluid may be temperature adjusted within the system to raise the temperature above ambient temperature or reduce the temperature below ambient temperature. The system can also maintain the surgical fluid at an elevated or reduced temperature relative to ambient temperature until the surgical fluid is ready to be used during a procedure. In use, the surgical fluid may be withdrawn from the basin and dispensed over a surgical site on or in a patient to irrigate the site and flush away bodily matter.

In some example, a drape according to the disclosure includes a thermoformed basin and side sheet bonded to the thermoformed basin. The thermoformed basin can be shape-indexed to the shape of a basin of a surgical system. The thermoformed basin may be formed of a polymeric material and may be sufficiently thin so as to be collapsible. In some configurations, for example, the drape may be defined by a bottom wall and collapsible sidewall. To facilitate compact packaging, the sidewall and/or bottom wall of the drape can collapse into a substantially flat package. After being removed from the package, however, the sidewall and/or bottom wall can expand to define the shape-indexed basin portion of the drape, which is insertable into the basin of the thermal treatment system. In this way, the drape can define a compact package for transport and/or storage yet expand to include a basin portion that would occupy more space if not collapsible.

Although a drape according to the disclosure can have a variety of different features as described herein, in some configurations, the drape includes a flexible window portion. The flexible window portion may be thermally bonded between a thermoformed basin portion and flexible side sheet portion of the drape. The window portion can be positionable over a user input device (e.g., display screen) of the thermal treatment system over which the drape is deployed. The window portion may be formed of a polymer that is visually transparent to the user. Depending on the type of polymer used, the polymer may contain a tackifying agent to increase the tackiness and/or friction of the window (e.g., as compared to other portions of the drape). The can help prevent the window from sliding relative to the user interface over which the window is positioned when the user interacts with the user interface through the window.

As another example feature, the drape may include an electronically readable tag embedded in the drape. For example, the electronically readable tag may be positioned in a pocket formed by bonding two sheets of material together. The electronically readable tag may be oriented relative to the basin portion such that, when the drape is placed over the thermal treatment system, the electronically readable tag is positioned over a non-contact reader. This arrangement can provide a securely attached electronically readable tag that is appropriately positioned relative to the thermal treatment system by inserting the basin portion of the drape into the basin of the thermal treatment system without requiring special positioning by the operator.

In one example, a drape for a surgical fluid thermal treatment system is described. The drape includes a flexible sheet having a basin portion and a side sheet portion connected to the basin portion. The basin portion defines a bottom wall and a collapsible sidewall. The collapsible sidewall is configured to transform from a first configuration in which the basin portion is expanded such that the basin portion is configured to conform to a basin of the surgical fluid thermal treatment system to a second configuration in which the basin portion is collapsed and the flexible sheet is planar.

In another example, a drape is described that includes a thermoformed basin that is shape-indexed to a shape of a basin of a surgical system into which the thermoformed basin is configured to be inserted. The example specifies that the thermoformed basin is collapsible. In addition, the example specifies that the drape includes flexible side sheet bonded to and extending about an entire perimeter of the thermoformed basin.

In another example, a method is described that includes removing a drape that is folded and flat from a sealed package. The method includes inserting a basin portion of the drape into a basin of a surgical fluid thermal treatment system and expanding the basin portion of the drape from a collapsed configuration to an expanded configuration.

In another example, a method of folding a drape is described. The method includes providing a drape that includes a collapsible basin and a flexible side sheet extending about a perimeter of the collapsible basin, the flexible side sheet having a first edge and a second edge on an opposite side of the flexible side sheet from the first edge. The method involves arranging the drape so the collapsible basin is collapsed and substantially planar and folding the first edge of the drape toward the second edge of the drape to form a first fold line transecting the collapsible basin. The method further involves folding the first edge of the drape back away from the second edge of the drape to form a second fold line offset form the first fold line, thereby providing a first drape panel positioned over the collapsible basin. In addition, the method includes folding the first edge of the drape toward the second edge of the drape to form a third fold line offset from the second fold line, and folding the first edge of the drape back away from the second edge of the drape to form a fourth fold line offset form the third fold line, thereby providing a second drape panel positioned over the collapsible basin.

The details of one or more examples are set forth in the accompanying drawings and the description below. Other features, objects, and advantages will be apparent from the description and drawings, and from the claims.

BRIEF DESCRIPTION OF DRAWINGS

FIGS. 10-26 illustrate example folding and packaging steps that may be utilized for a drape according to the disclosure.

DETAILED DESCRIPTION

Figure 1:
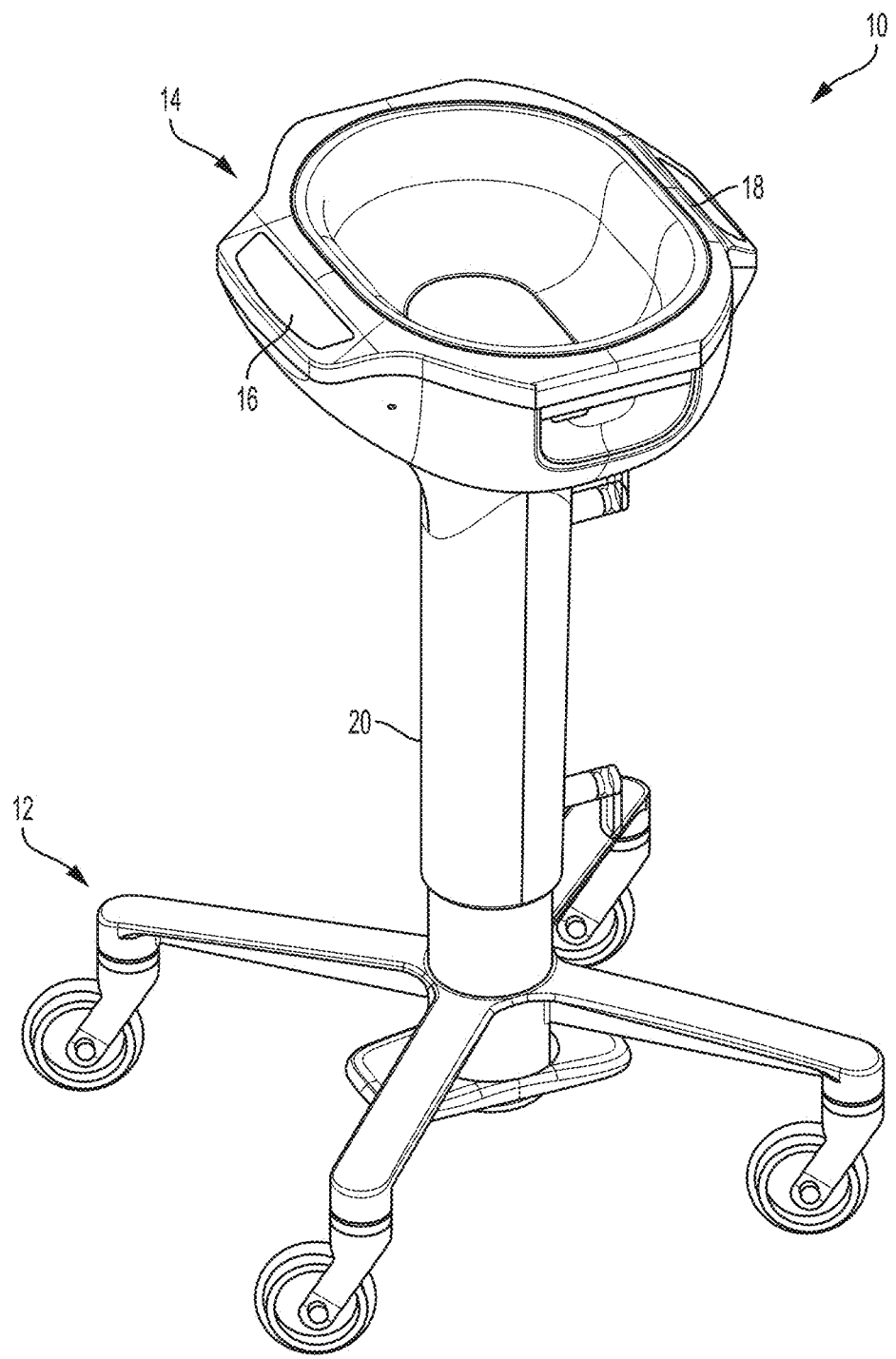
FIG. 1 is a perspective view of an example surgical system that may be draped with a drape according to the disclosure.

This disclosure is generally directed to drapes used to protect medical equipment. In some examples, a drape according to the disclosure is individually pre-packaged and is sterilized so as to be free from bacteria or other living organisms. The drape may be subject to thermal treatment and/or chemical treatment (e.g., exposed to ethylene oxide) to provide a sterilized drape that can be arranged over medical equipment within an operating environment to establish a sterile field over the medical equipment so draped. The drape can be disposed after use and a new drape used during a subsequent medical procedure or, in the case of a long procedure, during a latter portion of the same medical procedure.

In some examples, a drape is configured with a basin portion and a side sheet portion. The side sheet portion can be operatively connected to the basin portion and, in some configurations, extend outwardly away from the basin portion. The entire drape may be formed of flexible sheet material(s) that can be can be deformed under human hand pressure. For example, the drape may be folded into a compact, substantially flat package with the basin portion collapsed in on itself and the side sheet portion folded over the collapsed basin. In use, an operator can remove the drape from the package and insert the collapsed basin portion over a corresponding piece of medical equipment to be draped. The operator can expand the collapsed basin portion into its expanded shape, substantially conforming the walls of the basin portion to the corresponding piece of medical equipment to be draped. The side sheet portion may drape downwardly over the piece of medical equipment. By configuring the drape with a collapsible basin, among other features, a more compact package may be provided for transport and storage than if a drape structure was fabricated by attaching a flexible plastic drape around a rigid basin.

While a drape according to the disclosure can be used to drape any type of equipment that is desirably covered during use, the drape may be particularly useful to drape equipment used within a medical environment to provide a sterile draped surface over the equipment. Reference to a medical, surgical, or operating environment includes any hospital, clinic, facility or location where illness or injuries are diagnosed or treated using interventional or non-interventional techniques. Example pieces of medical equipment that may be draped using a drape with a basin portion according to the disclosure include, but are not limited to, a sink basin, a weighing trough to weight materials introduced into or removed from a patient, a basin to hold material used during a surgical procedure (e.g., tools, swabs), and the like.

As one specific example, a drape may be deployed over a system for thermally treating surgical fluid before utilizing the fluid during a medical procedure. The surgical fluid may be temperature adjusted within the system to raise the temperature above ambient temperature or reduce the temperature below ambient temperature. The system can also maintain the surgical fluid at an elevated or reduced temperature relative to ambient temperature until the surgical fluid is ready to be used during a procedure.

FIG. 1 is a perspective view of one example of a system 10 for thermally treating surgical fluids that may be draped with a drape according to the disclosure. In the example, of FIG. 1, system 10 includes a base 12 and a basin 14. Basin 14 is supported by and vertically elevated above base 12. Basin 14 can provide an open reservoir into which surgical fluid can be dispensed or other material being processed introduced. Once added to basin 14, the surgical fluid can be temperature adjusted within the basin. For example, basin 14 may be thermally coupled to a thermal treatment device that can raise or lower the temperature of thermal fluid. Basin 14 can also maintain surgical fluid at a target temperature until the fluid is removed from the basin and used in a procedure. In some configurations, system 10 can heat surgical fluid in basin 14 to a temperature near a patient's normal body temperature, such as a temperature within the range of 90 degrees Fahrenheit (32.2 Celsius) to 120 degrees Fahrenheit (48.9 Celsius), such as from 95 degrees Fahrenheit (35 Celsius) to 105 degrees Fahrenheit (40.6 Celsius).

To allow an operator to interact with system 10 and control different settings, system 10 may include a user interface. In the example of FIG. 1, system 10 includes at least one user interface 16. User interface 16 can include a user input through which a clinician inputs information to system 10 and a user output from which the clinician receives information from the system. For example, user interface 16 may include one or more manipulable inputs that the clinician can interact with to adjust settings of system 10, provide an indication that fresh fluid is being added to basin 14, provide an indication that non-surgical components are being added or removed from system 10, change a temperature to which fluid in basin 14 is heated, or the like. The manipulable user input may be implemented as physically depressible buttons (e.g., switches), portions of a touch screen that a clinician can interact with, or other features that a clinician can interact with to convey information to system 10. The user output of user interface 16 may be a display that provides graphical and/or textual information concerning the operation of system 10.

In applications where system 10 includes a display, the system can be configured with a single display or multiple displays. In FIG. 1, system 10 is illustrated as having a first display that forms part of user interface 16 and a second display 18. The first display is positioned on an exterior surface of one side of basin 14 while the second display is positioned on an exterior surface on a substantially opposite side of the basin. This arrangement can be useful to allow clinicians working on different sides of basin 14 to see information regarding the operation of system 10. In some examples, second display 18 is part of a user interface that includes the same features and functionalities (e.g., user input(s) and/or user output(s)) as first user interface 16. This can allow the clinician to present information to and receive information from system 10 when working on either side of the system. In other examples, second display 18 may be a display that provide a user output but does not have user input controls. In these applications, the clinician may enter information or commands through user input(s) on user interface 16 but be able to view output information on both displays.

Any type of material may be introduced into and removed from basin 14 during a procedure, including any type of surgical fluid during a medical procedure. Example types of medical fluid that may be used during a medical procedure include water, saline, or the like. The surgical fluid may or may not include medicament, such as compounds imparting antibacterial properties, anticoagulation/coagulation properties, anesthesia properties, or the like. Alternative materials that may be introduced into basin 14 can include a medical specimen extracted from a patient for weighing (e.g., in embodiments in which basin is configured to measure weight), blood, platelets, or materials for thermal adjustment before being introduced into a patient, or non-medical related materials (e.g., in applications in which system 10 is not used in a medical environment). Additionally or alternatively, medical tools may be added and removed from basin 14 during use, such as an asepto bulb syringe and/or a graduated measuring container.

In the configuration of FIG. 1, basin 14 is supported by and vertically elevated above base 12. In particular, basin 14 is mounted on an elongated housing 20 that extends vertically upwardly from base 12. Base 12 and housing 20 can elevate basin 14 to a position where it is convenient for a clinician to interact with the basin. Additional details on example thermal treatment systems can be found in U.S. patent application Ser. No. 15/469,476, filed Mar. 24, 2017, the entire contents of which are incorporated herein by reference.

Figure 2:
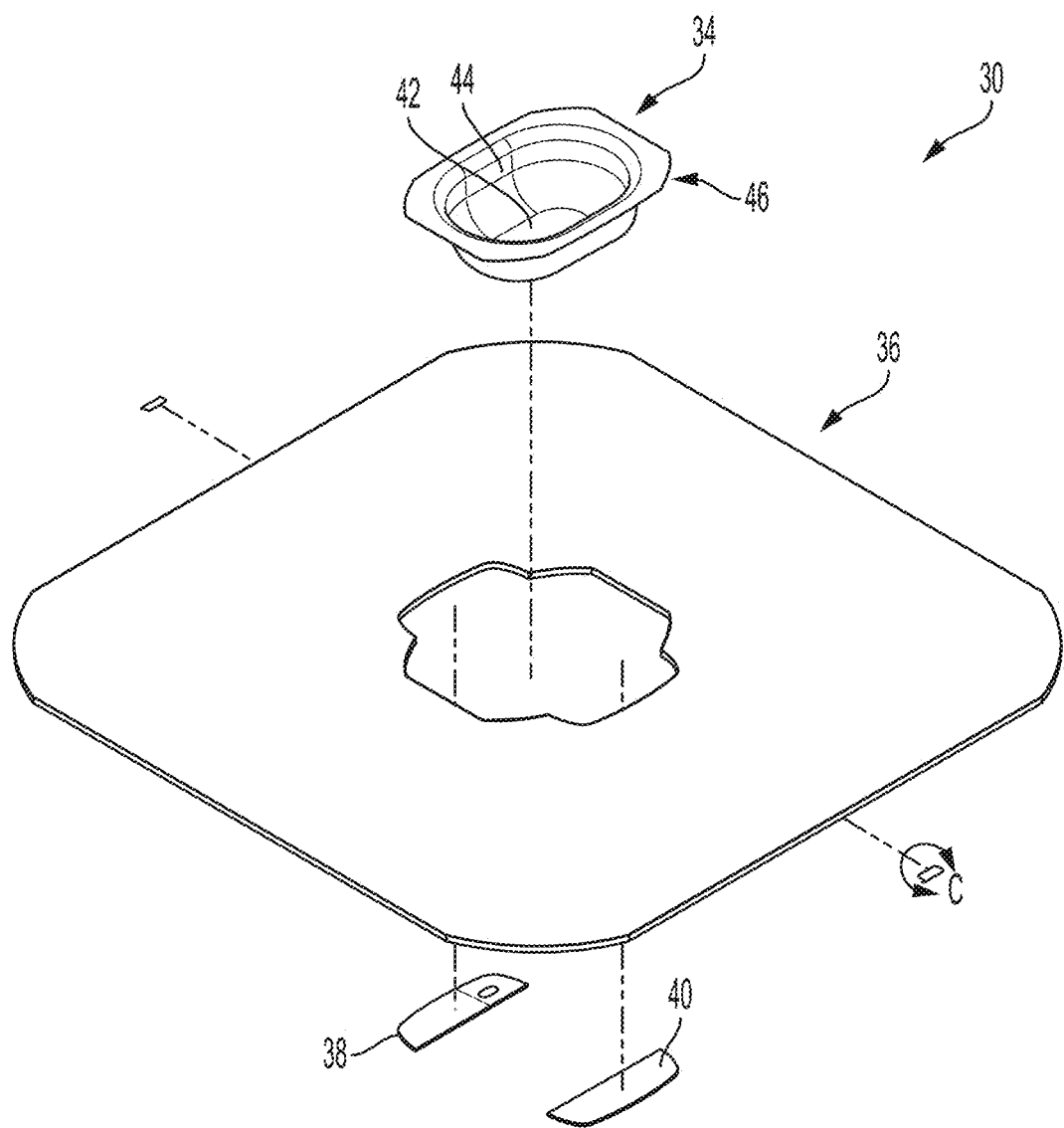
FIGS. 2 and 3 are perspective illustrations of an example drape.
Figure 3:
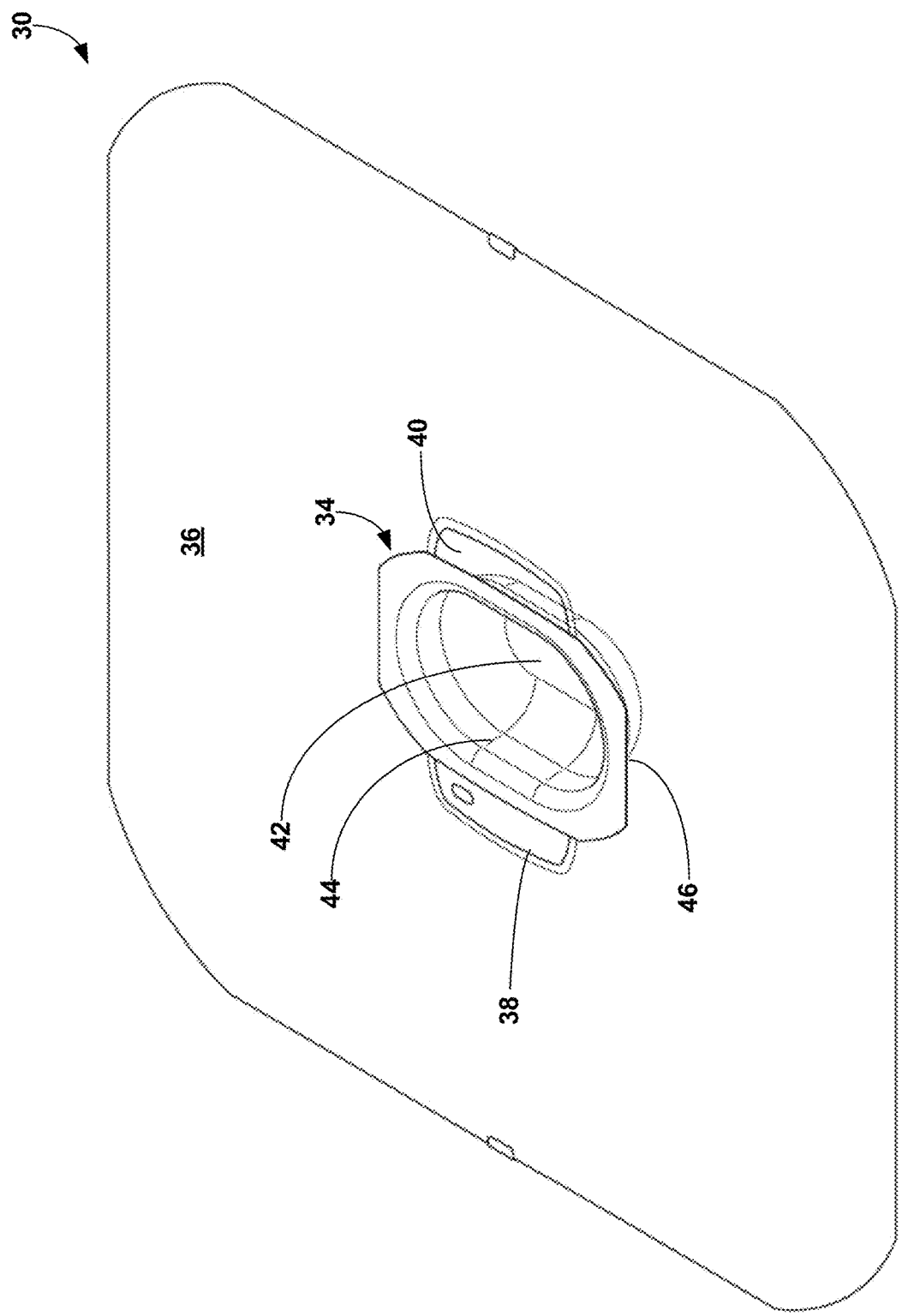

Independent of the configuration of the equipment to be draped, a drape according to disclosure can have a variety of different features and configurations as discussed herein. FIGS. 2 and 3 are perspective illustrations of an example drape 30 that may be used to drape system 10 in FIG. 1 or any other desired piece of equipment. FIG. 2 is an exploded perspective view of drape 30, while FIG. 3 illustrates the drape in assembled form. As shown, drape 30 can be formed from a flexible sheet of material 32 that has a basin portion 34 and side sheet portion 36. Side sheet portion 36 can at least partially, and in the illustrated example entirely, surround the perimeter of basin portion 34. Side sheet portion 36 can be physically connected to basin portion 34 to define a unitary, unbroken sheeting surface. In some configurations such as that illustrated in FIGS. 2 and 3, drape 30 includes one or more window portions 38, 40. The window portions 38, 40 of drape 30 may be arranged and designed to be positioned over viewable and/or interactable features of the equipment being draped, such as user interface 16 and/or display 18 in system 10 of FIG. 1.

Basin portion 34 of drape 30 can be collapsible to facilitate flat folding and packing of drape 30 and expandable to facilitate insertion of the basin portion into a basin to be draped during use. Basin portion 34 in FIGS. 2 and 3 is illustrated in an expanded configuration where the basin portion defines its maximum volume, e.g., such as the configuration when the drape is in use and basin portion 34 of drape 30 is inserted into basin 14 of system 10. Basin portion 34 of drape 30 can be collapsible so that the basin portion folds down into a more compact shape and is substantially planar (e.g., FIG. 7).

Basin portion 34 of drape 30 may define a reservoir that receives and holds surgical fluid or other materials inserted into the equipment being draped with the drape positioned therebetween. Basin portion 34 of drape 30 can define any polygonal (e.g., rectangle, square, hexagonal) or arcuate (e.g., circular, elliptical) shape, or even combinations of polygonal and arcuate shapes. In the illustrated example, basin portion 34 is shown as a general oval shape and includes a bottom wall 42 and at least one sidewall 44 extending vertically upwardly away from the base (e.g., when basin portion is expanded and not collapsed). Bottom wall 42 and sidewall 44 can collectively form a bounded cavity with an open top surface that receives and holds materials inserted into the covered equipment with the drape positioned between the equipment and the material.

Side sheet portion 36 of drape 30 can be connected to basin portion 34 and extend outwardly and/or downwardly away from the basin portion. For example, basin portion 34 may define a perimeter 46 that delimits the basin portion. The perimeter 46 of basin portion 34 may be where the basin portion transitions from a vertical-orientated sidewall defining a reservoir depth or height (e.g., when in the expanded configuration) to a horizontally-oriented sidewall. In either case, side sheet portion 36 can be physically connected to perimeter 46 of basin portion, e.g., either directly or indirectly with a window 38, 40 positioned between the perimeter and the side sheet. Side sheet portion 36 can be flexible and fall or drape downwardly under the force of gravity over the equipment which the drape is installed. For example, when drape 30 is deployed over system 10 in FIG. 1, basin portion 34 can be inserted into basin 14 of the system with side sheet portion 36 draping downwardly over at least a portion of the exterior surface of basin 14 and/or housing 24.

In general, basin portion 34 of drape 30 may be shape-indexed to the shape of the basin or reservoir into which basin portion 34 is intended to be inserted. Basin portion 34 may be shape-indexed in that it may have a complementary size and/or shape to the reservoir or basin of the equipment to be draped and into which basin portion 34 is intended to be inserted. For example, basin portion 34 may be shape-indexed so that bottom wall 42 and sidewall 44 are in physical contact with and/or conform to corresponding wall surfaces of the structure into which the draped basin portion is inserted (e.g., basin 14 of system 10 in FIG. 1). Conforming the shape of basin portion 34 to the structure into which it is intended to be inserted can be useful, e.g., to facilitate efficient thermal transfer between the heated or cooled wall surfaces of the structure and the material contained within basin portion 34 whose temperature is being adjusted.

The shape of basin portion 34 can be established by the configuration of bottom wall 42 and the at least one sidewall 44. In general, sidewall 44 extends upwardly from bottom wall 42. The number of sidewalls interconnected together to form the side structure of basin portion 34 can vary depending on the shape of the reservoir. For example, a basin portion with a circular cross-sectional shape (e.g., in the horizontal plane) may be formed of a single sidewall whereas a basin portion with a square or rectangular cross-sectional shape may be defined by four interconnected sidewalls.

In some examples, the at least one sidewall 44 defining basin portion 34 is sloped such that the sidewall extends vertically upwardly and outwardly away from bottom wall 42. For example, sidewall 44 may be curved and define a radius of curvature where the sidewall intersects and joins bottom wall 42. Bottom wall 42 may be flat, curved, or have other suitable shape profile. Configuring sidewall 44 with a curved or sloped profile instead of a straight sidewall may help prevent materials from accumulating in corners where sidewall 44 intersects bottom wall 42. For example, basin portion 34 may define an arcuate shape devoid of 90 degree angles to help prevent materials from accumulating in such angular regions. That being said, in other examples, sidewall 44 may not be curved but may instead be straight (e.g., perpendicular with respect to ground).

Figure 4:
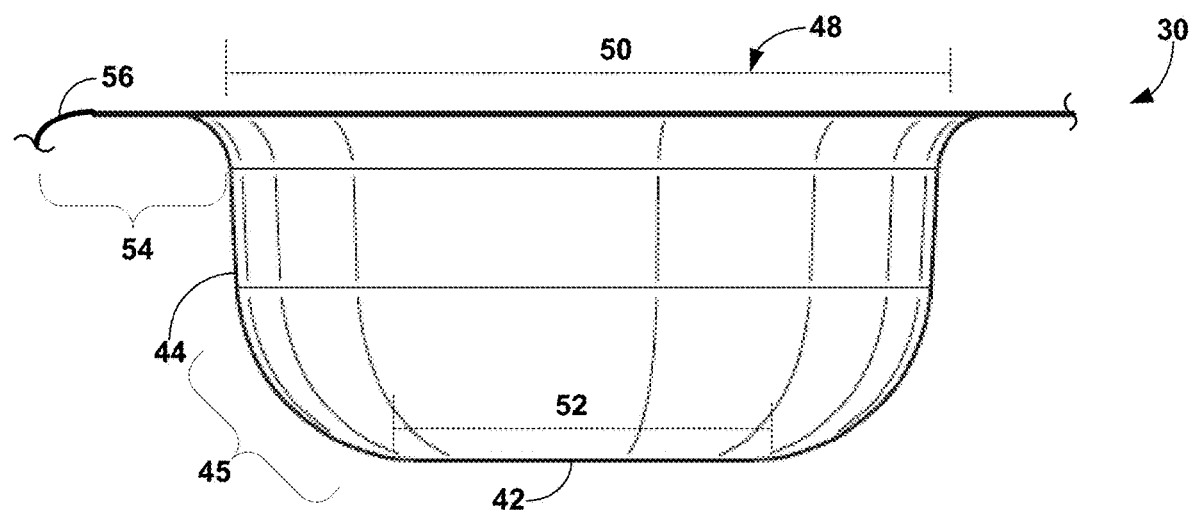
FIGS. 4 and 5 are a side view and perspective view, respectively, showing an example layout of a basin portion that can be used for the drape of FIGS. 2 and 3.
Figure 5:
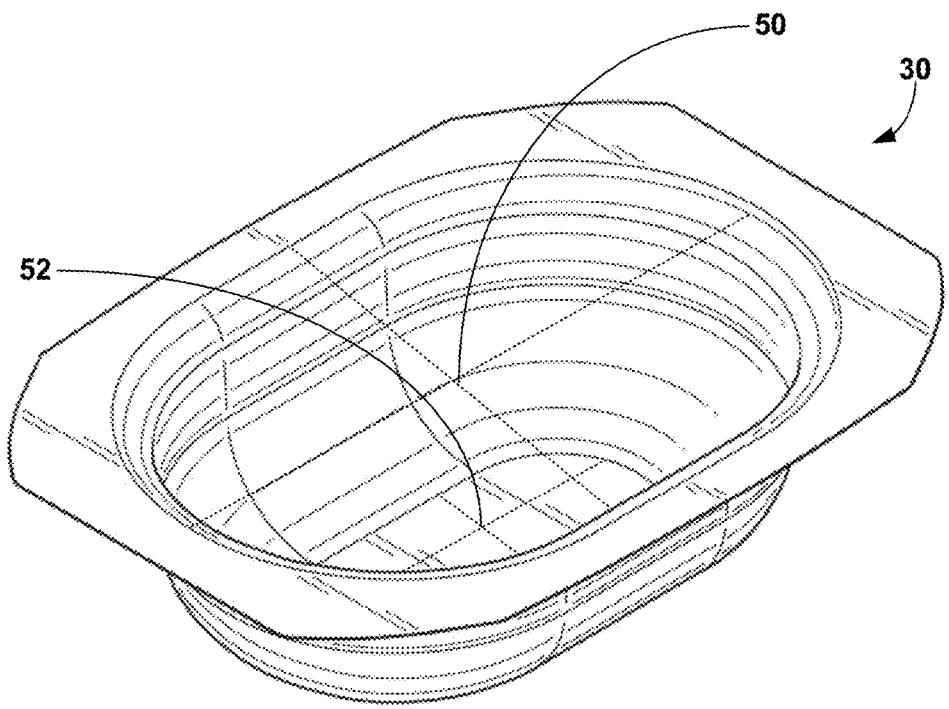

FIGS. 4 and 5 are a side view and perspective view, respectively, of basin portion 34 showing an example layout of the basin portion. As shown in this example, sidewall 44 defines a radius of curvature 45 where the sidewall extends outwardly from and joins to bottom wall 42. When so configured, basin portion 34 may define an open top surface 48 that has a greater cross-sectional area 50 then the cross-sectional area 52 defined by bottom wall 42. Configuring basin portion 34 so the open top surface 48 defined by the basin portion is larger than bottom wall 42 may be useful to provide space for the basin portion to collapse into a compact profile. For example, basin portion 34 may collapse telescopically such that bottom wall 42 is arranged substantially coplanar with perimeter 46 and sidewall 44 is nested or folded in rings of collapsed/gathered material between the bottom wall and upper end of the sidewall.

In some configurations, such as the configuration illustrated in FIGS. 4 and 5, sidewall 44 extends vertically upwardly from bottom wall 42 and defines a curved perimeter lip 54. The curve perimeter lip 54 may be a transition region of sidewall 44 that transitions from a generally vertical orientation to a generally horizontal orientation. In some examples, curved perimeter lip 54 of basin portion 34 may transition sidewall 44 from a generally upward vertical orientation, to a generally horizontal orientation, and then to a generally downward vertical orientation. For example, sidewall 44 may extend upwardly from bottom wall 42 to an inflection point 56 and then extend downwardly from the inflection point toward ground (e.g., when installed over the object being draped). The weight of side sheet portion 36 hanging down toward ground under a force of gravity may help impart this curvature to the perimeter lip of basin portion 34. Configuring basin portion 34 with a curved perimeter lip may be useful to help the basin portion wrap over the top surface of the basin or reservoir of the equipment being draped with drape 30.

Although drape 30 is illustrated as having a single basin portion 34 for being inserted into a corresponding basin of equipment being draped, the drape may be formed with multiple basin portions separated from each other by a wall of material. For example, basin portion 34 may be a single cavity with internal partition(s) or divider(s) separating one or more reservoir cavities from fluid communication with one or more other reservoir cavities. Alternatively, drape 30 may include multiple basin portions 34 separated from each other but physically joined together.

As mentioned above, drape 30 may include at least one window portion which, in the example of FIGS. 2 and 3, is illustrated as two window portions 38, 40. Each window portion may be a transparent region that is configured to be positioned over user interface features of the equipment being draped. For example, drape 30 may include a first window portion 38 configured to be positioned over user interface 16 of system 10 (FIG. 1) and a second window portion 40 configured to be positioned over display 18 of system 10. By configuring drape 30 with transparent window portions 38, 40, a user can better visualize and/or interact with equipment features located under the respective window portion.

When drape 30 includes a window portion, the location of the window portion relative to basin portion 34 may vary depending on the configuration of the equipment intended to be draped. In some examples, drape 30 includes at least one window portion positioned between basin portion 34 and side sheet portion 36. The window portion can be connected to basin portion 34 and side sheet portion 36, collectively forming an unbroken drape surface.

Figure 6:
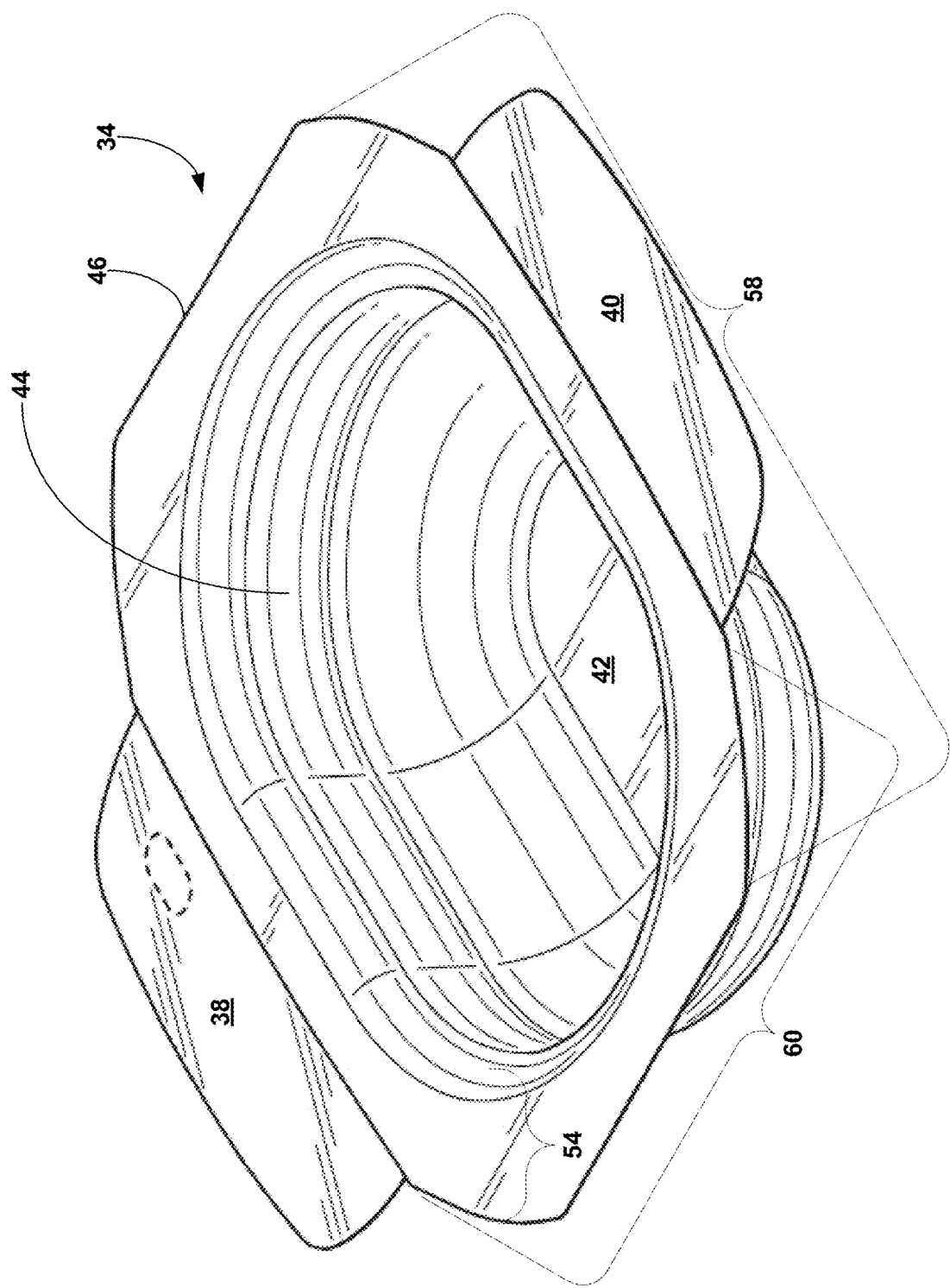
FIG. 6 is a perspective view showing an example arrangement of window portions relative to a basin portion that can be used for the drape of FIGS. 2 and 3.

FIG. 6 is a perspective view of basin portion 34 showing an example arrangement of window portions 38 and 40 relative to the basin portion. As shown, basin portion 34 defines a perimeter 46 having a length 58 and a width 60. In the illustrated configuration, first window portion 38 projects away from one lengthwise perimeter section of basin portion 34. Second window portion 40 projects away from the opposite lengthwise perimeter section of basin portion 34. In this arrangement, no window portion projects away from the widthwise perimeter sections of the basin portion, although other window arrangements can be used without departing from the scope of disclosure.

In the arrangement of FIG. 6, basin portion 34 is illustrated as defining an oval-shaped cavity formed, collectively, by bottom wall 42 and sidewall 44. The oval-shaped cavity transitions to a generally rectangular shape about perimeter 46. For example, perimeter lip 54 of sidewall 44 is illustrated as transitioning from the oval cross-sectional shape to the generally rectangular cross-sectional shape. The corners of the generally rectangular perimeter shape for basin portion 34 are illustrated as being chamfered or rounded, although may intersect at sharp (e.g., 90°) angles in other configurations.

Although drape 30 can be fabricated from any suitable materials, the drape may typically be fabricated from one or more polymeric materials. Example polymers that may be used to fabricate drape 30 include, but are not limited to, polyethylene, polypropylene, polyvinyl chloride, polystyrene, polyamide, polytetrafluoroethylene (PTFE), polyethylene terephthalate (PET), polyurethane, and combinations thereof.

The specific material or materials used to form drape 30 may be selected based on the desired performance characteristics of the drape, such as its chemical and/or thermal resistance, its puncture resistance, its flexibility, or yet further performance characteristic. For example, where drape 30 is intended to cover a piece of equipment that adjust the temperature of the contents placed in basin portion 34 relative to ambient temperature, at least basin portion 34 may be selected for temperature compatibility with the equipment being draped. In some examples, drape 30 and/or basin portion 34 of the drape may be formed of a polymer having a melt temperature rater than 100° F., such as greater than 120° F., greater than 130° F., or greater than 150° F. This may be useful for draping over a thermal warmer, such as the example thermal warmer illustrated in FIG. 1, in applications where the contents placed in basin portion 34 are heated around the temperature of the human body or slightly above that temperature.

In some examples, each portion of drape 30 (e.g., basin portion 34, side sheet portion 36, and windows 38, 40) are formed of the same polymer. In other examples, at least one portion of drape 30 may be formed of a different polymer composition then at least one (and optionally all) of the other portions forming the drape. For example, basin portion 34 may be formed of a first polymer composition, windows 38, 40 may be formed of a second polymer composition, and side sheet portion 36 may be formed of a third polymer composition. The first, second, and third polymer compositions may each be different from each other. For example, each polymer composition may be formed from different types of monomers, or multiple (e.g., all) of the polymer compositions may be formed from the same type of monomer with different constituent ingredients included in the formulation to provide a different resulting composition.

As one example, the first, second, and third polymer compositions may each be formed from a polyurethane monomer but may having different formulations to provide compositions different from each other. The pre-polymerization resins used to fabricate the first, second, and third polymer compositions may contain a common polyurethane monomer but may include different additives and/or constituent ingredients. Additionally or alternatively, the type and/or degree of polymerization may vary between the different polymer compositions used to fabricate the different portions of drape 30.

In some examples, the second polymer composition used to fabricate window portions 38, 40 is selected to have tackier surface properties than the first polymer composition used to fabricate basin portion 34 and the third polymer composition used to fabricate side sheet portion 36. For example, the second polymer composition may have a tackifying agent (e.g., in different amounts and/or a different composition than in the first and third polymer compositions) that impacts the tackiness of window portions 38, 40. Example tackifying agents that may be used include, but are not limited to, aliphatic hydrocarbon resins; rosin esters and rosin acids; mixed aliphatic/aromatic tackifying resins; polyterpene tackifiers; and hydrogenated tackifying resins, such as those produced from the polymerization and subsequent hydrogenation of aromatic feedstocks such as styrene, alpha-methyl styrene, and vinyl toluene.

Fabricating window portions 38, 40 from a polymeric composition that imparts tackiness and/or resistance to sliding friction may be useful to facilitate user interaction with the portion of the draped equipment underlying window portions 38, 40. The comparatively greater tackiness of window portions 38, 40 than basin portion 34 and/or side sheet portion 36 may be useful to help prevent the window portions from moving if a user presses against one of the window portions to interact with equipment features under the window portion. For example, where a window portion overlies a user interface of a draped piece of equipment, a user may press against the window portion to engage the user interface covered by the window portion. In some examples, the material(s) used to fabricate the window portions of drape 30 exhibits a coefficient of friction according to ASTM D1894 greater than 1 and/or may be too tacky to test according to the standard.

Depending on the type of material(s) selected to fabricate the different portions of drape 30, the different portions may have any degree of optical transparency ranging from transparent to opaque, in each case within the visible light spectrum. For example, drape 30 or any portion thereof may be transparent, translucent, or opaque. In some examples, window portions 38, 40 are transparent, and side sheet portion 36 is transparent or translucent. This configuration can help a user see features and/or components of the equipment draped under the window portions and/or side sheet portion. Additionally, any portion of drape 30 may or may not be colored, e.g., by incorporating a dye or pigment in a polymeric composition forming the drape. Drape 30 or a portion thereof, such as side sheet portion 36, may be blue to help visually designate that the drape is defining a sterile area.

When drape 30 is formed from one or more polymeric materials, polymeric processing techniques may be used to fabricate the drape or any portion thereof. For example, drape 30 may be formed using casting, extrusion, calendaring, and/or other polymeric processing technique. In some examples, drape 30 or any portion thereof is formed from an extruded polymeric film, which may be a single layer film or multilayer film of the same or different chemical constituents.

Additionally or alternatively, basin portion 34 of drape 30 may be formed using a thermoforming technique to produce a thermoformed basin. Thermoforming generally involves heating a plastic sheet until it is pliable (e.g., optionally above the glass transition temperature) and stretching it over a mold having the inverse shape of the shape desired to be imparted into the sheet being thermoformed. The polymeric sheet can have the shape of the mold imparted into it upon cooling, e.g., resulting in a thermoformed basin portion 34. The thermoforming process may occur under vacuum pressure or positive pressure. When performing vacuum thermoforming, a plastic sheet may be heated until it is pliable (e.g., optionally above the glass transition temperature) and then vacuum drawn down into a mold having the same shape as the shape desired to be imparted into the sheet being thermoformed.

While basin portion 34 of drape 30 may be formed using other polymer shaping techniques, such as injection molding, blow molding, or rotational molding, thermoforming may be useful to produce a basin portion that has a thinner thickness than would result if using other polymer shaping techniques. Basin portion 34 of drape 30 may collapse more readily to facilitate packing and storage when it is formed of a thinner gauge material than if it is formed of a thicker gauge material that does not collapse into a planar shape.

While drape 30 and each portion thereof may be formed of any suitable thickness material, in some examples, basin portion 34 is fabricated from a thicker material than the side sheet portion 36. Fabricating basin portion 34 from a thicker material may be helpful to prevent surgical tools or other potentially sharp objects placed in basin portion 34 during use from puncturing the drape. By contrast, fabricating side sheet portion 36 from a comparatively thinner material may increase the flexibility of the side sheet portion, helping the side sheet portion drape downwardly over the object covered by drape 30.

In some configurations, basin portion 34 has a thickness ranging from 0.05 mm to 1 mm, such as from 0.1 mm to 0.5 mm. Side sheet portion 36 may have a thickness less than 0.2 mm, such as less than 0.15 mm, or less than 0.05 mm. For example, side sheet portion 36 may have a thickness ranging from 0.025 mm to 0.15 mm, such as from 0.05 mm to 0.08 mm. A window portion of drape 30 (such as window portions 38, 40, when included) can have a thickness substantially equal to that of side sheet portion 36, basin portion 34, or yet a different thickness. For example, the window portion(s) of drape 30 may have a thickness that is thinner than that of the side sheet portion 36 and/or basin portion 34. The window portion(s) may have a thickness and be constructed of a material that allows a screen and/or buttons under the window to be tactile and feelable to a user pressing the screen and/or buttons through the window. In some examples, window portion(s) of drape 30 may have a thickness ranging from 0.05 mm to 0.1 mm. The thickness of each portion of drape 30 may be constant across the drape or may vary across the drape.

Figure 7:
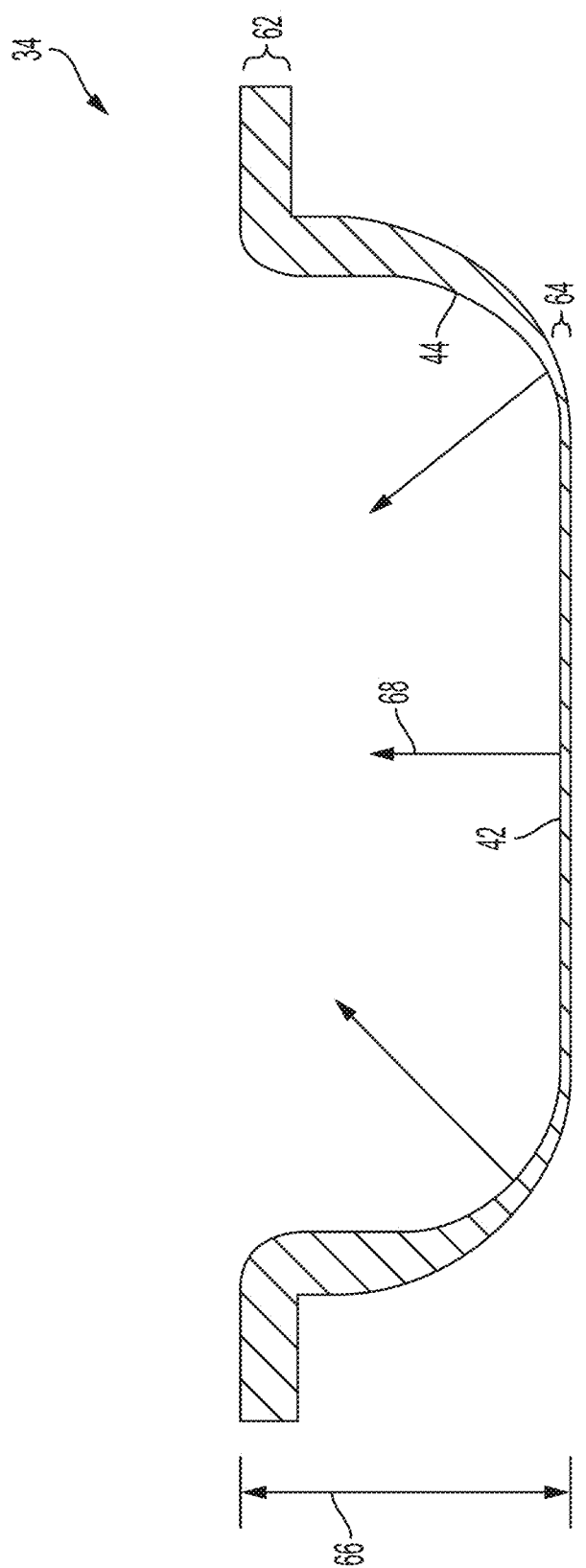
FIG. 7 is a sectional view illustrating an example configuration of a basin portion where the thickness of the basin portion varies.

FIG. 7 is a sectional view of basin portion 34 illustrating an example configuration of the basin where the thickness of the basin varies. In this example, basin portion 34 defines a maximum thickness 62 at its perimeter edge 46. The thickness of the material forming basin portion 34 tapers to a minimum thickness 64 at bottom wall 42. Although FIG. 7 illustrates the thickness of material progressively and continuously decreasing in thickness along sidewall 44 between perimeter edge 46 and bottom wall 42, in other configurations, the taper may be discontinuous or may be to a different extent than illustrated in the example figure. The material forming basin portion 34 may be tapered during the thermoforming process as the polymeric sheet used to form the basin portion is stretched to assume the basin shape. This can result in a thinning of material over the region in which the basin depression is defined as compared to the substantially horizontal/planar perimeter edge of the basin portion, which may be substantially un-deformed through the thermoforming process.

In some examples, the thickness of sidewall 44 varies from a maximum thickness 62 equal to or greater than 0.4 mm to a minimum thickness 64 where the sidewall joins bottom wall 42 less than 0.4 mm. For example, the maximum thickness 62 of sidewall 44 may range from 0.4 mm to 0.7 mm. The minimum thickness 64 of sidewall 44 may range from 0.1 mm to 0.2 mm. Accordingly, a ratio of a maximum thickness divided by a minimum thickness of the basin portion 34 may range from 2 to 10, such as from 3 to 5, although other thickness ratios may be used.

Independent of whether the thickness of sidewall 44 of basin portion 34 is constant or varies, the thickness may be sufficiently small so as to allow the sidewall of the basin portion to collapse. Sidewall 44 may collapse by deforming the sidewall under human hand pressure, causing the sidewall to loose structural rigidity and fold or crumple upon itself. The sidewall 44 may be reversibly expanded by applying an expansion force under human hand pressure opposite the deformation force, causing the folded or crumpled sidewall to elongate and/or stretch out to assume its stretched, wall-like structure. In different examples, bottom wall 42 of basin portion 34 may be rigid or may be as flexible and collapsible (or even more so) than sidewall 44.

In practice, drape 30 may be fabricated from a single sheet of material (which may itself be a single layer of material or multiple layers of material integrally bonded together, such as through co-extrusion) or may be fabricated from different sections of material joined together. For example, each portion of drape 30 (e.g., side sheet portion 36, basin portion 34, windows 38, 40) may be formed separately (e.g., from separate sections of material) and joined together to form drape 30. Alternatively, drape 30 may be formed from a single, unitary sheet of material in which basin portion 34 is formed to define the drape. Accordingly, while the different portions of drape 30 are described as being connected together herein, it should be appreciated that the portions may be physically connected by being part of a common sheet of material or may be physically connected by bonding different sheets or sections of material together to form drape 30.

In some examples, each portion of drape 30 (e.g., side sheet portion 36, basin portion 34, windows 38, 40) are formed from separate sections or sheets of material, e.g., each of which has a different polymeric composition. Each portion of drape 30 may be cut to a size suitable for incorporation into the resulting drape, e.g., with the edge of the cut portion overlapping an adjacent portion to form a bond therebetween. Any suitable bonding technique can be used to join different portions of drape 30 together to form the resultant drape structure. For example, different portions of drape 30 may be bonded together using an adhesive and/or thermal bonding, such as ultrasonic bonding, RF bonding, laser bonding, or other bonding technique which uses heat to melt and integrally join overlapping sections of polymeric material to form a bond there between.

In general, the specific dimensions of drape 30 and each portion thereof may vary depending on the configuration of the equipment intended to be covered by the drape. Basin portion 34 of drape 30 can define a height 66 (FIG. 7) that varies depending on whether the basin is in its fully expanded form (deployed use state) or whether it is in its fully collapsed form (packaged state). In some examples, the height 66 of basin portion 34 ranges from 75 mm to 150 mm when the basin is fully expanded. By contrast, when basin portion 34 is fully collapsed, the height of the basin portion may be less than 50 mm, such as less than 25 mm.

To collapse basin portion 34, bottom wall 42 and sidewall 44 may be folded up into the void space defined by the basin portion in its otherwise expanded state, as indicated by arrows 68 on FIG. 7. For example, bottom wall 42 of basin portion 34 may be pushed upward and/or side sheet portion 32 pushed downward relative to the basin portion until the bottom wall is substantially coplanar with the side sheet portion. In the process of moving bottom wall 42 to be substantially coplanar with side sheet portion 36, sidewall 44 may collapse inwardly to also be substantially coplanar with the bottom wall and side sheet portion. As a result, the cavity defined by basin portion 34 in its expanded state can be eliminated to provide a substantially flat or planar drape. This can facilitate further folding and/or packaging of the drape to provide a compact structure for storage.

Figure 8:
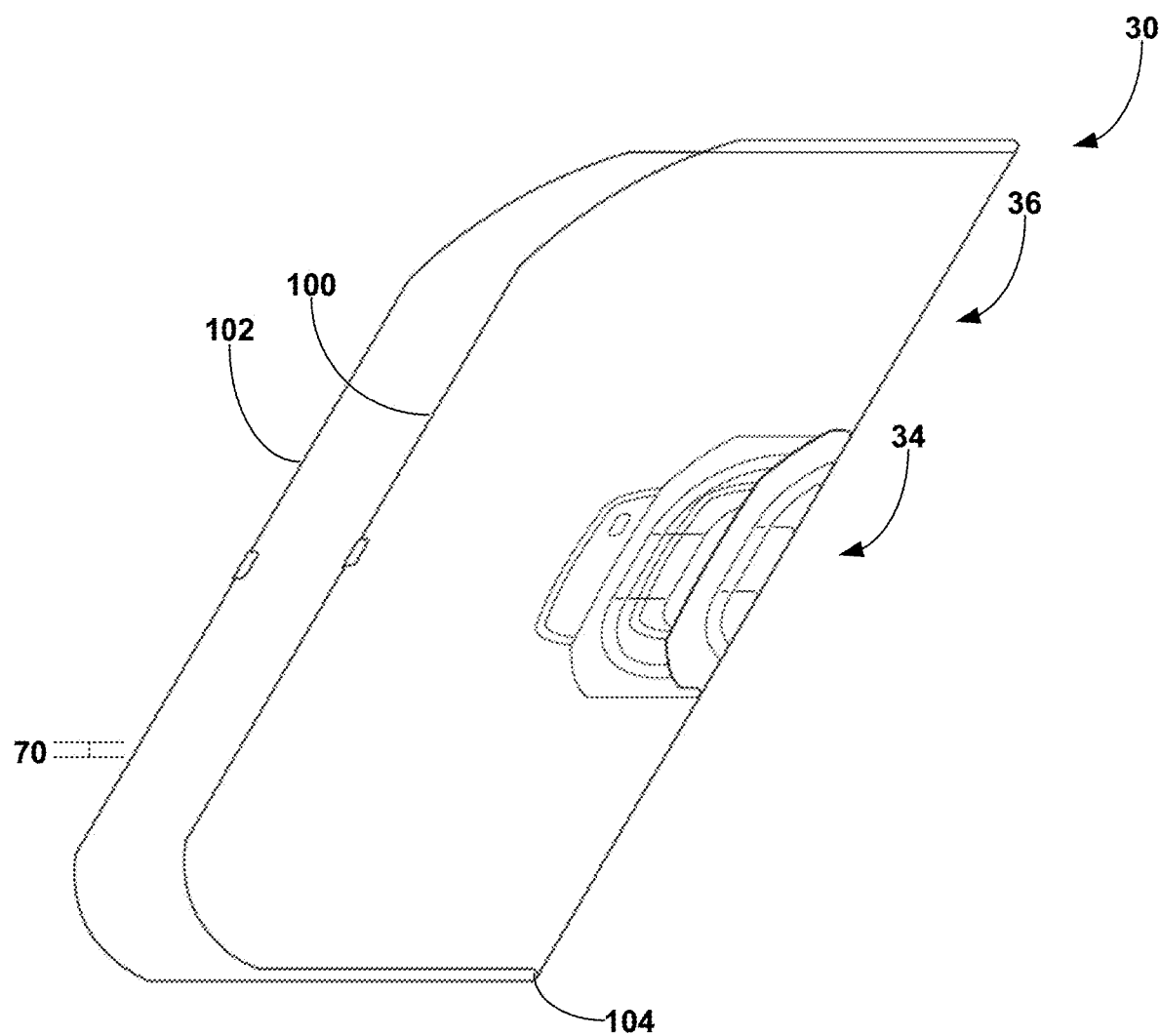
FIG. 8 is a perspective view showing an example collapsed configuration for the drape of FIGS. 2 and 3.

FIG. 8 is a perspective view of drape 30 shown with basin portion 34 collapsed to provide a planar flexible sheet. Depending on factors such as the thickness of the material(s) used to form drape 30 and the configuration of basin portion 34, drape 30 may define a height 70 less than 25 mm when basin portion 34 is collapsed, such as less than 10 mm, lesson 5 mm, or less than 1 mm. In some examples, height 70 ranges from 1 mm to 50 mm when basin portion 34 is collapsed, such as from 5 mm to 25 mm. The height 70 can be measured when basin portion 34 is collapsed and side sheet portion 36 is unfolded (e.g., as opposed to being stacked on top of the collapsed basin portion).

Drape 30 may include a variety of features to enhance the performance and/or functionality of the drape. As one example, drape 30 may include an electronically readable tag embedded in the drape. For example, the electronically readable tag may be positioned in a pocket formed by bonding two sheets of material together. The electronically readable tag may be positioned within any portion(s) of drape 30, e.g., to appropriately align the tag relative to the location of a corresponding non-contact electronic tag reader associated with the equipment being covered by drape 30.

Figure 9:
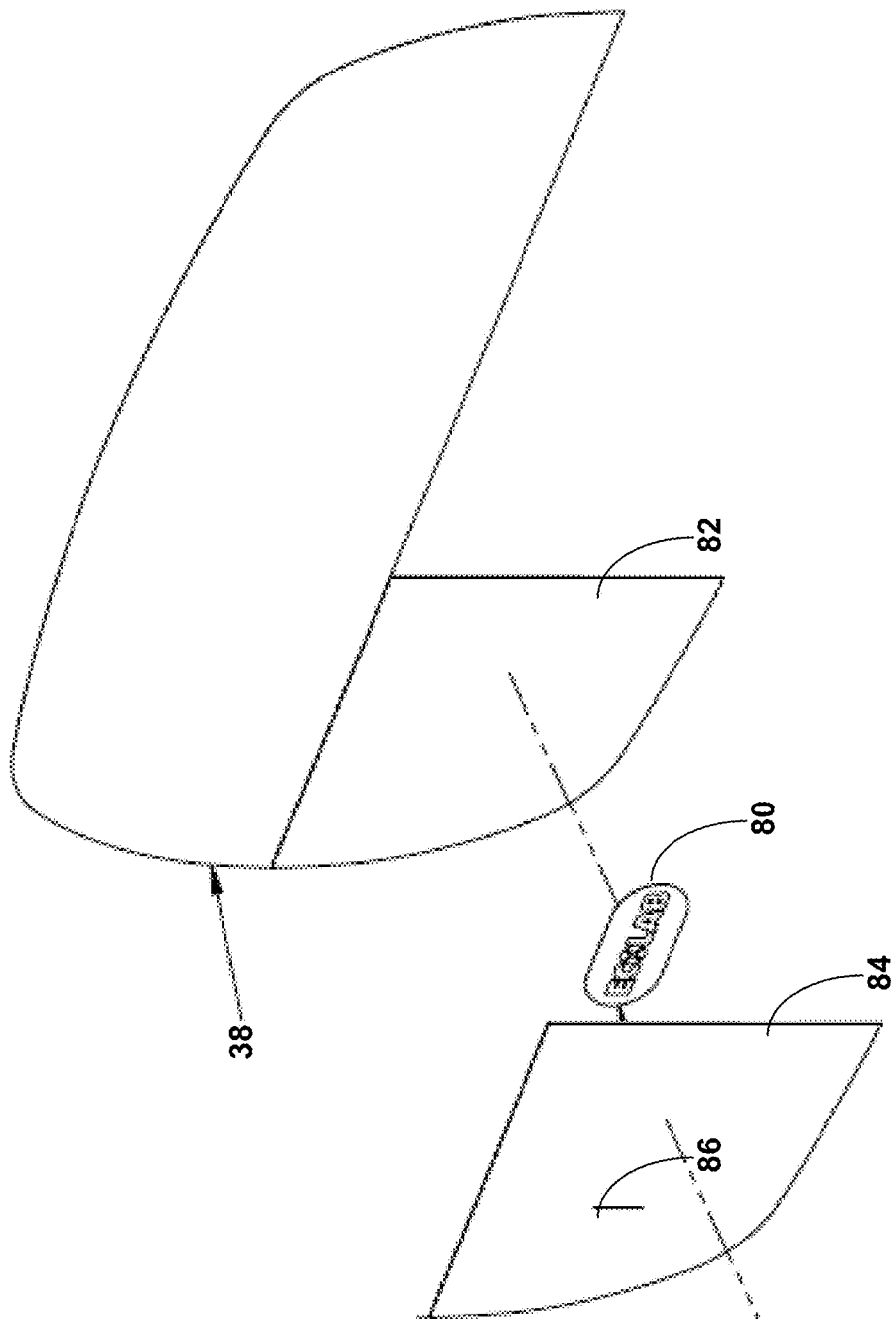
FIG. 9 is a perspective view of an example portion of a drape showing how an electronically readable tag may be arranged in the drape.

FIG. 9 is a perspective view of an example portion of drape 30 showing how an electronically readable tag 80 may be arranged in the drape portion. The illustrated example, tag 80 is positioned within a first window portion 38 of drape 30, although the tag may be positioned at other locations and/or in other portions of the drape without departing from the disclosure.

To secure and position electronically readable tag 80 in drape 30, the electronically readable tag 80 may be bonded between multiple layers of multiple. In the example of FIG. 9, for example, electronically readable tag 80 is illustrated as being positioned between a first layer of material 82 and a second layer of material 84. Each layer of material 82, 84 may itself be a single layer of material or multiple layers of material integrally bonded together, such as through co-extrusion, to form a composite layer having an inner face and an outer face. In either case, the first layer of material 82 and the second layer of material 84 can be bonded together, e.g., using any of the bonding techniques discussed above, to seal the electronically readable tag 80 in the space between the layers of material. The layers of material may be sealed and/or joined together directly up to the perimeter of the electronically readable tag 80 or may be joined together to form a pocket surrounding and separated from the perimeter edge of electronically readable tag 80.

In some examples, a small slit 86 (e.g., having a length less than the length of electronically readable tag 80) is formed through one of the layers of material between which the electronically readable tag 80 is positioned. Slit 86 can help during subsequent sterilization of drape 80, e.g., allowing a chemical sterilization gas such as ethylene oxide to flow into the space between the layers of material 82, 84 for sterilization.

Electronically readable tag 80 may be any type of non-transitory electronically readable medium and may be readable using a non-contact reader. In different examples, electronically readable tag 80 may be implemented using as a bar code, a radio frequency identification (RFID) tag, or a near field communication (NFC) tag. The electronically readable tag 80 may or may not be covered with a manufacturer or distributor logo or trademark, such as by placing a sticker bearing the trademark over the electronically readable tag 80.

As noted above, drape 30 may be sterilized to provide a sterile covering over the equipment draped for medical procedure. Drape 30 may be sterilized after fabrication, and optionally, after being packaged. To help ensure that drape 30 does not inadvertently become contaminated by an operator during the process of removing the drape from its packaging and deploying it over the equipment to be draped, drape 30 may be packaged so as to promote sterile and aseptic removal and deployment of the drape. For example, drape 30 may be folded and packaged in such a way that the user can remove the drape from its packaging and employ it over the equipment to be draped while minimizing or eliminating the extent to which the user touches the sterile, outward facing, surfaces of the drape defining the sterile field.

FIGS. 8 and 10-26 illustrate example folding and packaging steps that may be utilized to produce a folded drape that facilitates subsequent sterile removal and deployment. With reference to FIG. 8, drape 30 is illustrated as being arranged in a substantially planar or flat layout, which may be achieved by laying the drape out on a table surface for folding. Basin portion 34 is collapsed to be substantially planar with side sheet portion 36. As illustrated, drape 30 defines a first perimeter edge 100 and a second perimeter edge 102 on an opposite side of the drape from the first perimeter edge. In FIG. 8, the first perimeter edge 100 and the second perimeter edge 102 are lengthwise edges of a generally rectangular-shaped drape perimeter. In other examples, however, the perimeter edges used for folding may be width-wise edges of a drape having a rectangular-shaped perimeter, opposite side edges of a circular-shaped drape perimeter, or other edges defining the outward extent of the drape to be folded.

In the folding technique illustrated in FIG. 8, first edge 100 of drape 30 is folded towards second edge 102 of the drape to form a first fold line 104. The first fold line 104 may extend parallel to the basin portion 34. In some examples, first fold line 104 is offset from the basin portion 34 in a direction away from second edge 102. Additionally or alternatively, first fold line 104 may transect (e.g., cut across) basin portion 34. The first fold line may bisect basin portion 34 or, in the illustrated example, be offset from a bisecting centerline through basin portion 34 such that first edge 100 is not folded all the way to second edge 102.

Figure 10:
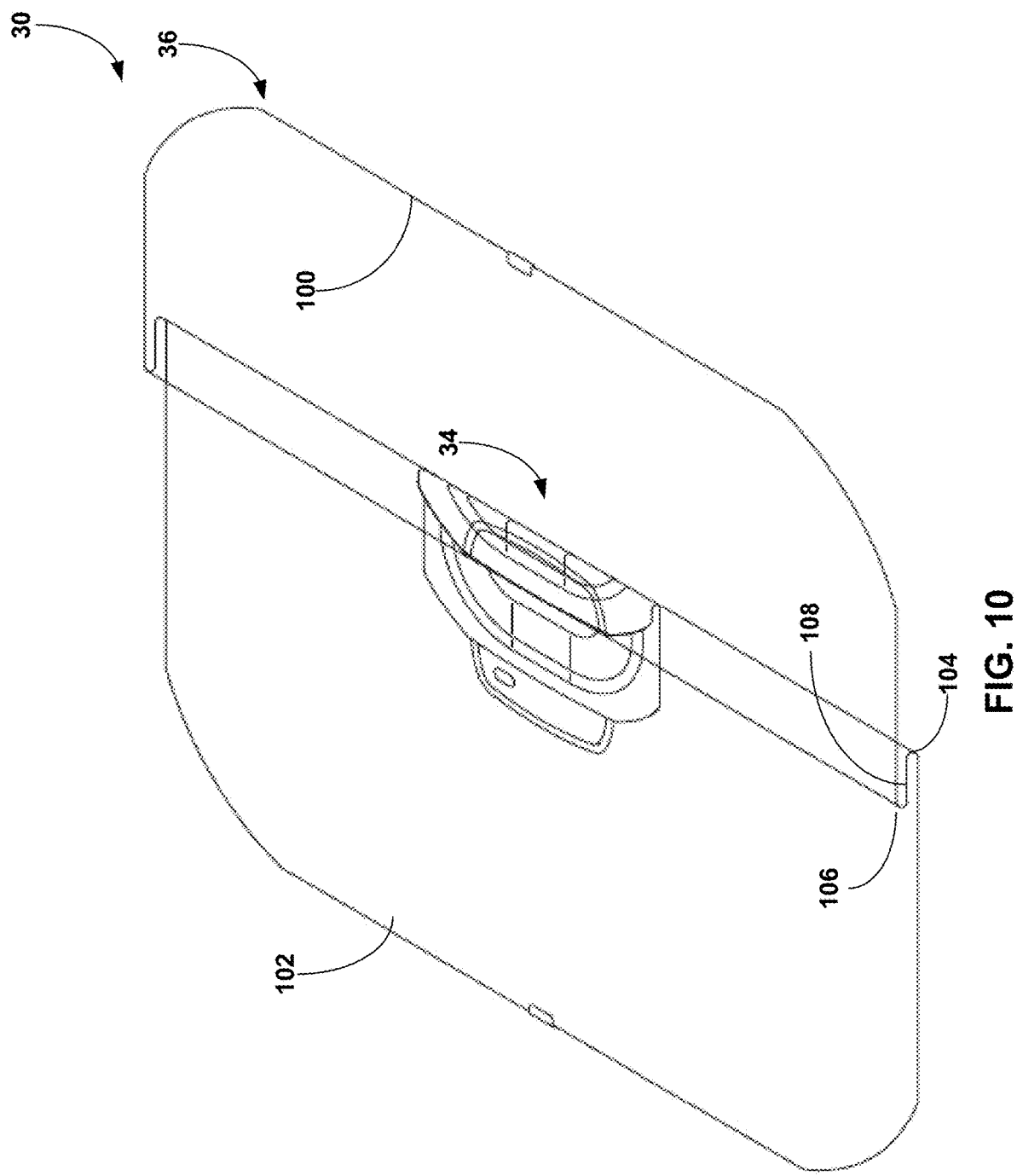

With reference to FIG. 10, the first edge 100 of drape 30 can be folded back away from second edge 102, for example in a direction opposite to the direction the first edge was initially folded toward the second edge. The first edge 100 may be folded back away from second edge 102 a lesser distance than the first edge 100 was previously folded toward the second edge 102. As a result, this can establish a second fold line 106 offset from the first fold line 104. The distance and/or drape material between the first fold line 104 and second fold line 106 can define a first drape panel 108, which may be a folded section of drape material. Depending on the position of first fold line 104 relative to basin portion 36, first drape panel 108 may be positioned at least partially, and in some examples fully, over the collapsed basin portion 36.

Figure 11:
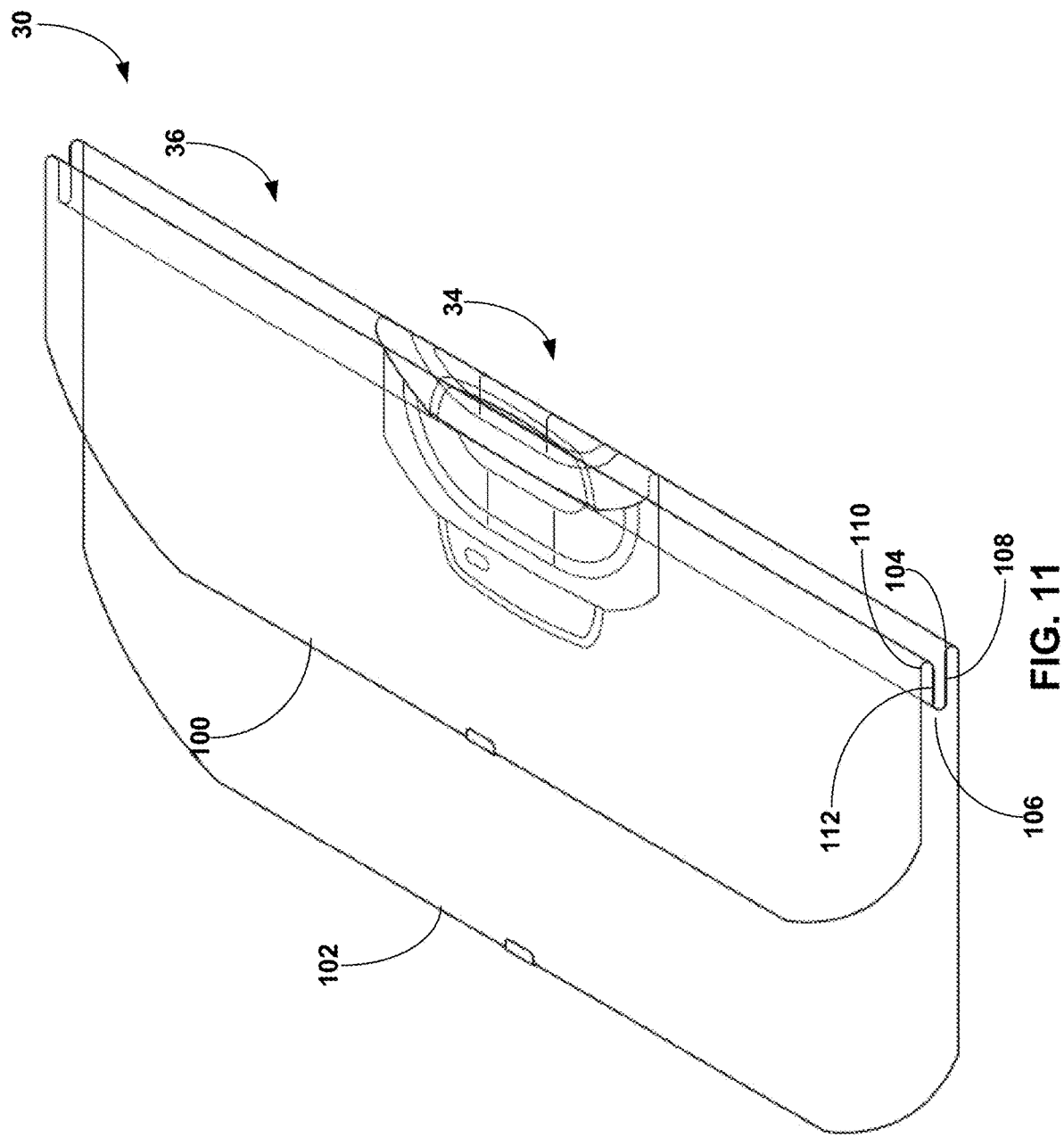
Figure 12:
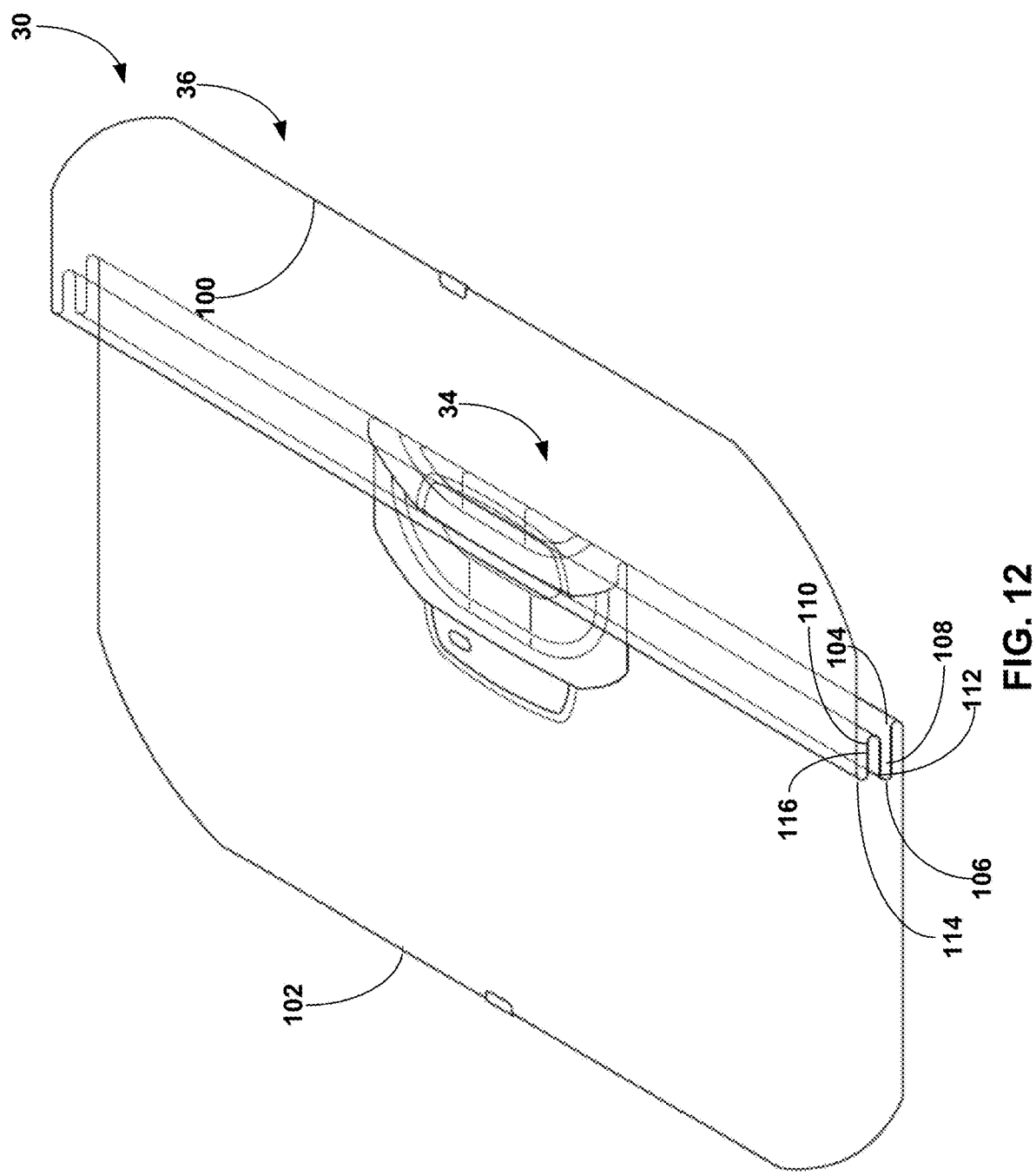
Figure 13:
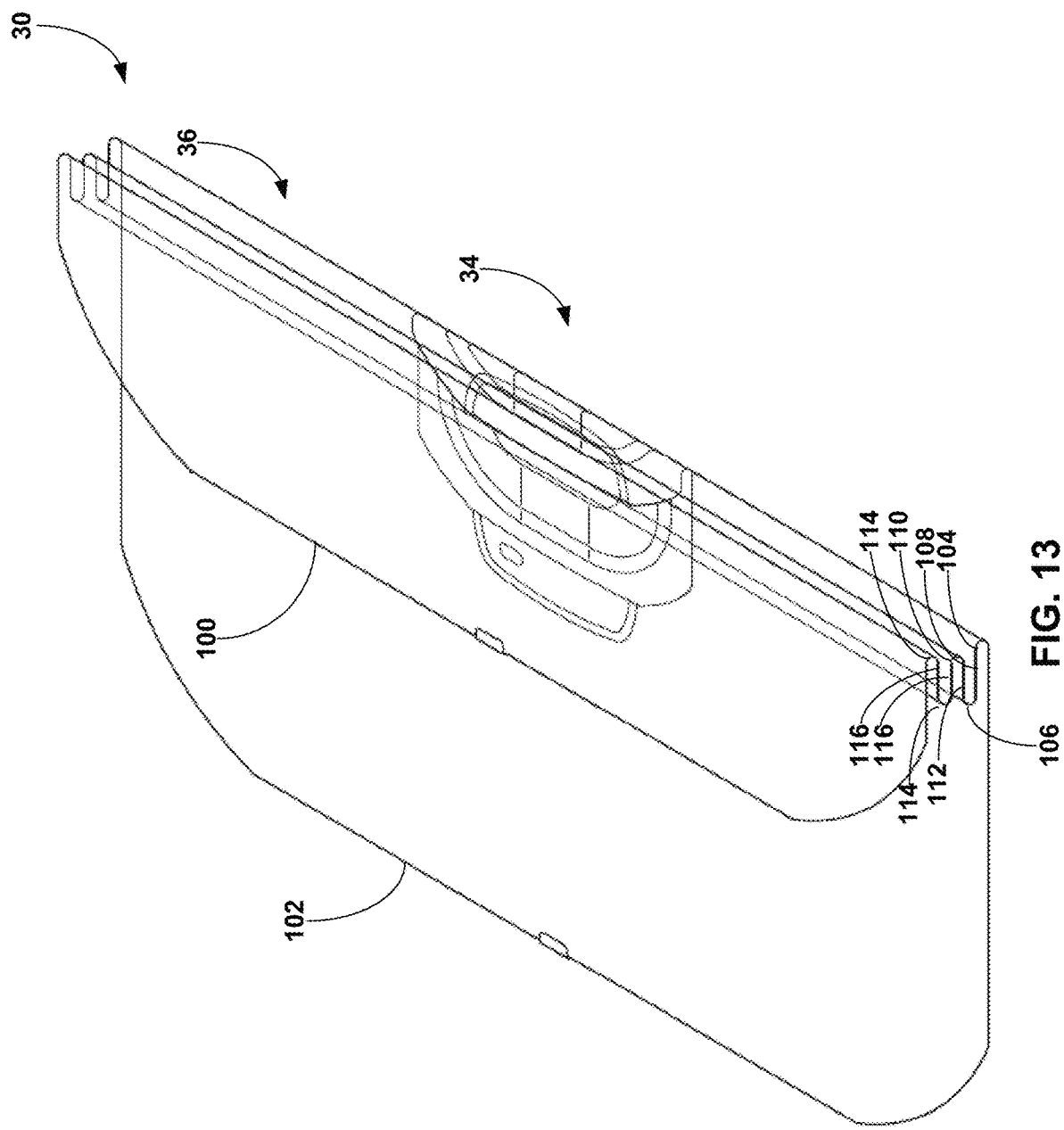
Figure 14:
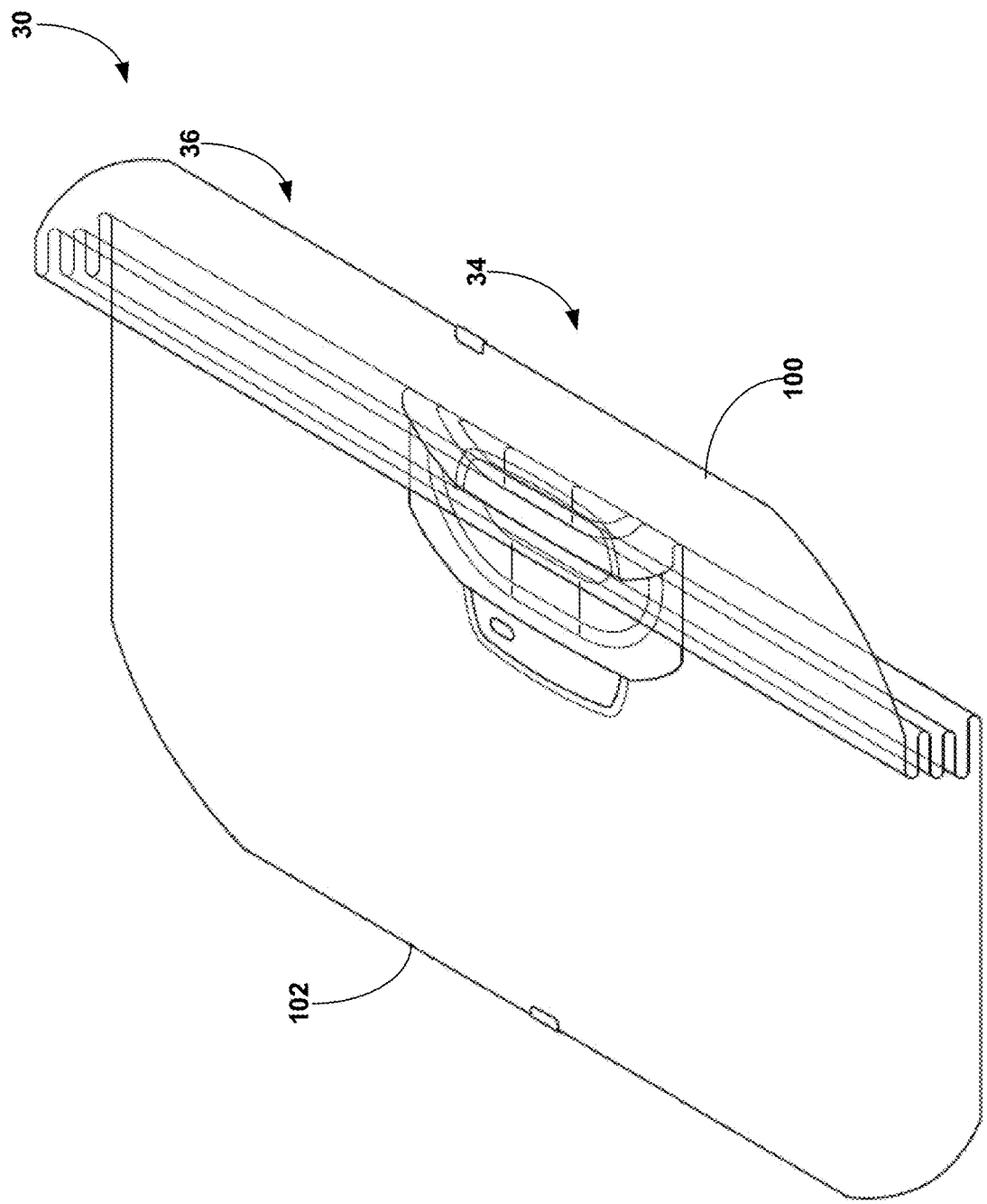
Figure 15:
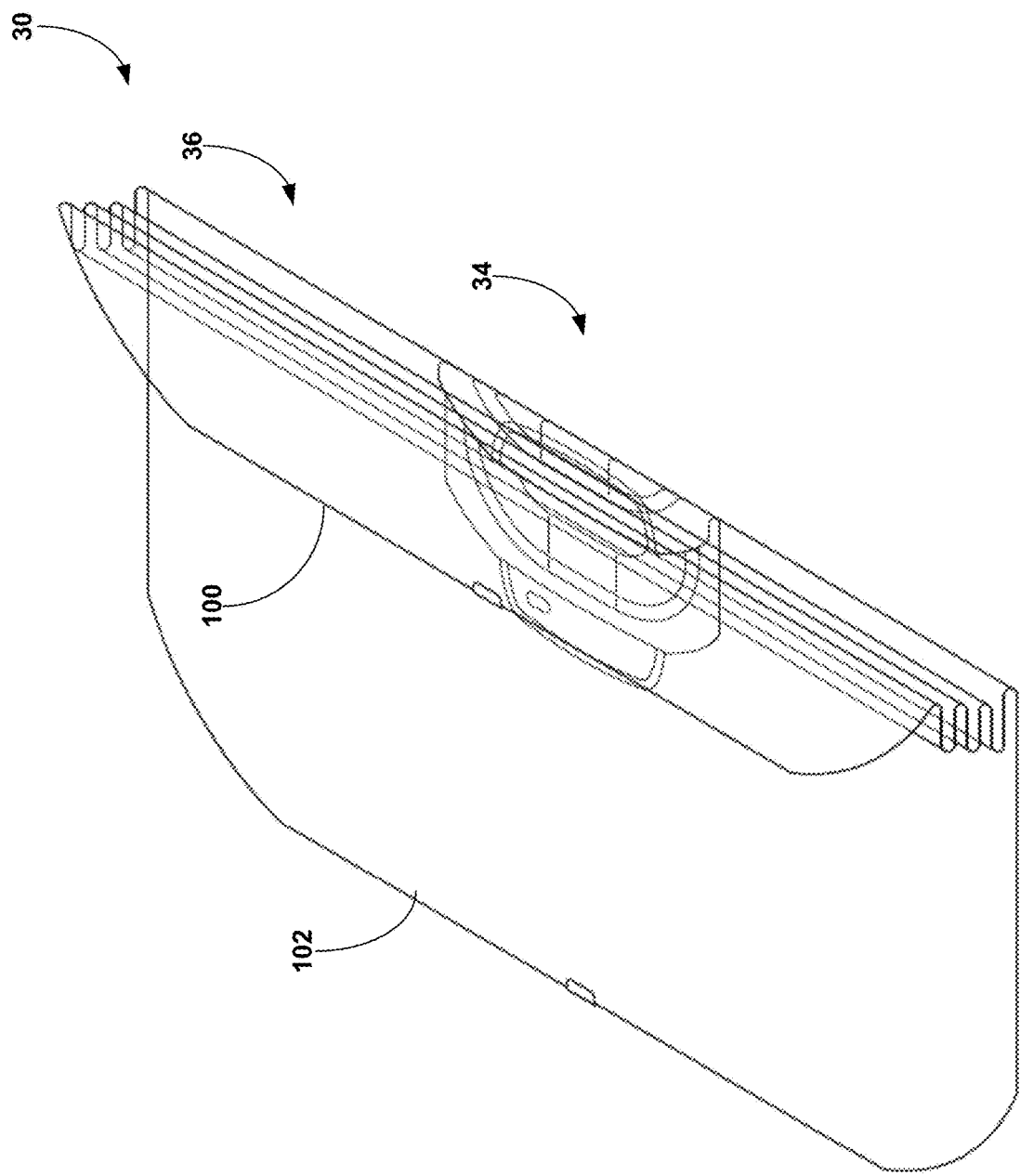
Figure 16:
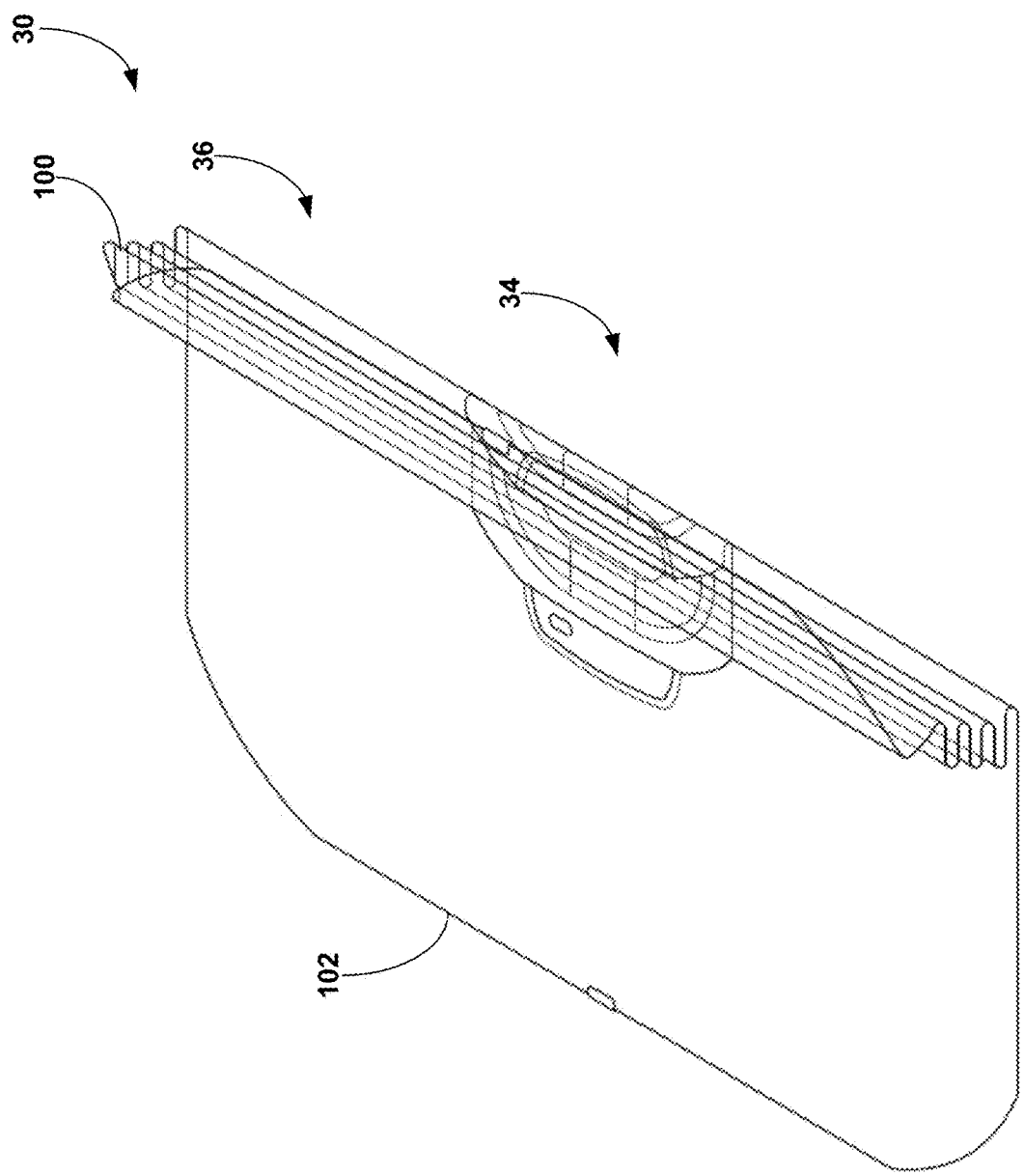
Figure 17:
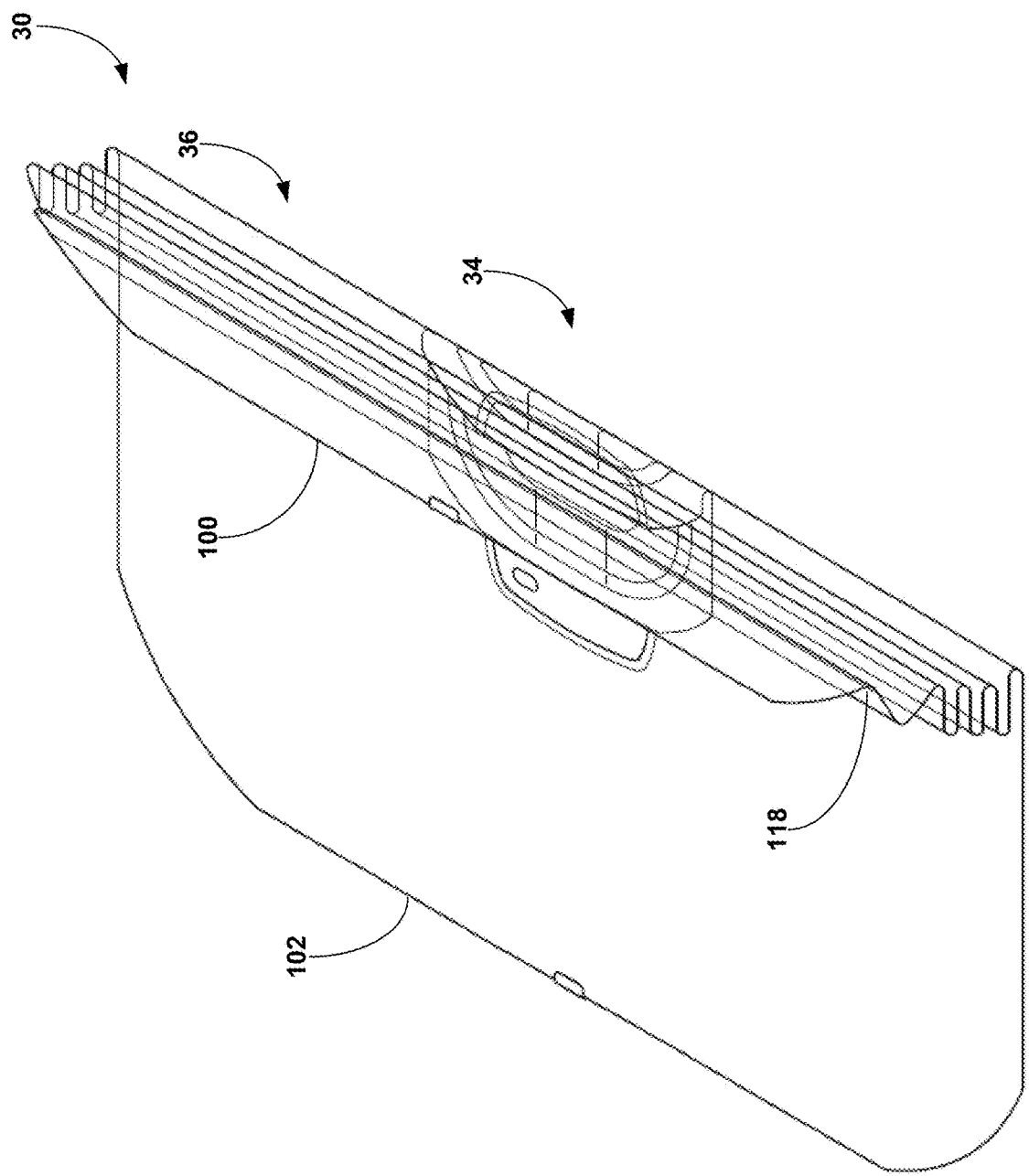

Continuing with FIG. 11, the first edge 100 of drape 30 may again be folded toward the second edge 102 of the drape. The first edge 100 may be folded toward second edge 102 a lesser distance than the first edge 100 was previously folded toward the second edge 102 to define a third fold line 110 offset from the second fold line 106. The distance and/or drape material between the second fold line 106 and third fold line 110 can define a second drape panel 112, which may be a second section of folded drape material. Again, depending on the position of second fold line 106 and third fold line 110, second drape panel 112 may or may not be positioned at least partially, and in some examples fully, over the collapsible basin portion 36. In different configurations, first panel 108 may have the same width as second panel 112 or may have a different width.

The process of folding the first edge 100 of drape 30 toward the second edge 102 and back away from the second edge to define additional fold lines, and correspondingly folded panels of material between the fold lines, can be repeated one or more (e.g., multiple) additional times. The number of folds and fold panels created during the folding process may vary, e.g., based on the size of the drape and the size of each panel created during the folding process. FIGS. 12-16 illustrate additional example folding steps that can be performed on drape 30 to define additional fold lines 114 and additional fold panels 116 between adjacent fold lines.

Once drape 30 has been folded a suitable number of times, the free edge of the drape (e.g., first perimeter edge 100) may be positioned for grasping by a user during subsequent deployment of the drape. In some examples, such as the example illustrated in FIG. 17, first edge 100 is folded toward second edge 102 to define a final fold line 118 and to position the first edge 100 over the collapsible basin portion 36. For example, first edge 100 may be folded toward second edge 102 so the edge is positioned on an axis bisecting basin portion 36.

Figure 18:
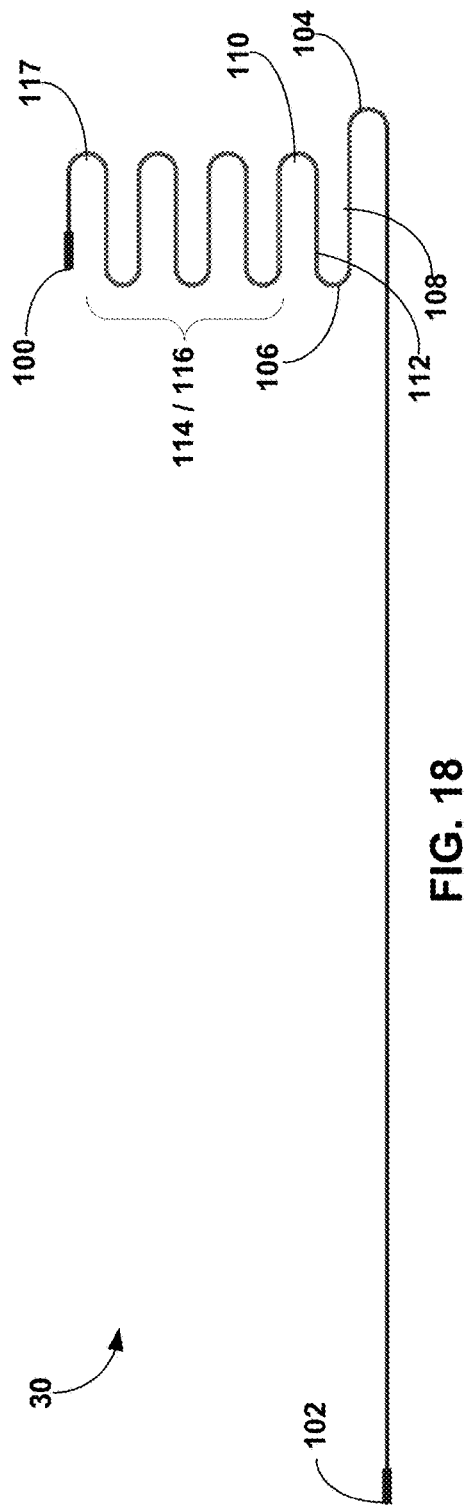

FIG. 18 is a side view illustration of drape 30 showing an example arrangement of fold lines and drape panel portions that may be formed through the process of folding the drape. The resultant folded drape section may have multiple drape panels stacked vertically on top of each other to define a stacked fold arrangement. In some examples, the cumulative number of drape panels in the vertical stack may range from 2 panels to 20 panels, such as from 5 drape panels to 15 drape panels. The drape panels may or may not be positioned over the collapsed basin portion 36. While the size of each panel may vary, in some examples, each panel ranges from 25 mm to 200 mm, such as from 50 mm to 100 mm.

Drape 30 in the illustrated example is shown as being symmetrical, such that side sheet portion 34 extends the same distance from basin portion 36 to first edge 100 as the side sheet portion extends from basin portion 36 to second edge 102. Accordingly, the folding process illustrated and described with respect to FIGS. 8 and 10-18 with respect to one half of the side sheet portion between basin portion 36 and first edge 100 may be replicated on the second half of side sheet portion 34, either concurrently with, prior to, or after folding the first half of the side sheet portion. In other configurations of drape 30, side sheet portion 34 may only extend from one side of basin portion 36, or may extend a different distance from the basin portion to the first edge 100 than the second edge 102. Accordingly, the number of folds and/or size of drape panels formed during folding may be the same on each side of basin portion 36 or may be different on different sides of the basin portion.

Figure 19:
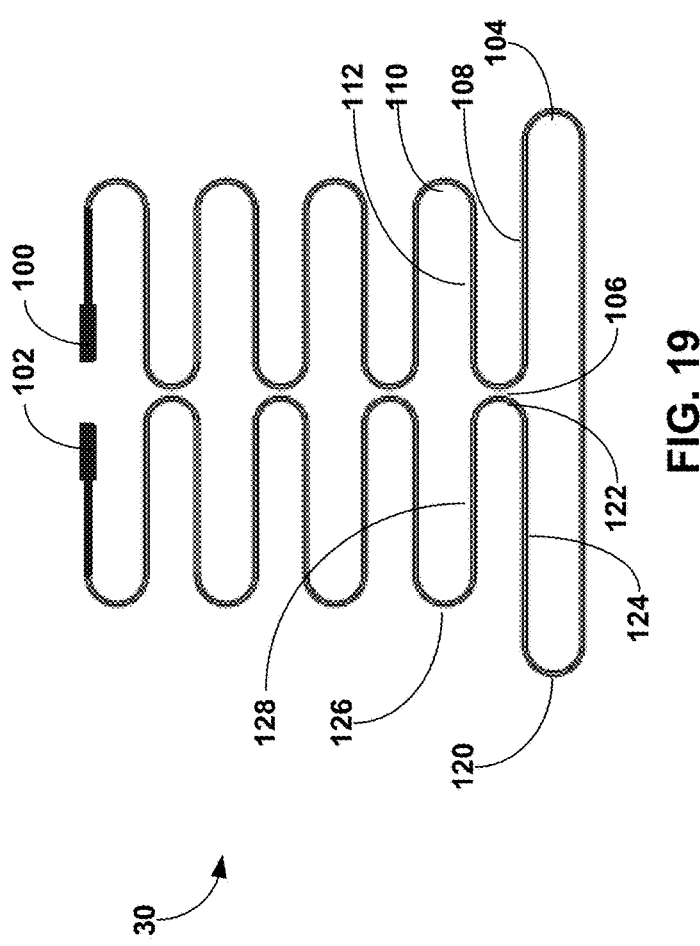

FIG. 19 is a side view illustration of drape 30 showing an example arrangement of fold lines and drape panel portions that may be formed through the process of folding both sides of the drape. As shown, both sides of drape 30 have been folded to define two vertically stacked sections of panel portions arranged side-by-side next to each other. The first stack of panel sections includes first fold line 104, second fold line 106, third fold line 110, etc. to form first drape panel 108, second drape panel 112, etc. The second stack of panel sections includes a fourth fold line 120, a fifth fold line 122, a sixth fold line 124, etc. to form a third drape panel 126, a fourth drape panel 128, etc.

In some examples, the first edge 100 of drape 30 and the second edge 102 of the drape are folded towards each other to create the outermost fold of the full drape. For example, the first edge 100 of drape 30 and second edge 102 of the drape may be brought into adjacent alignment, and in some examples abutting contact. The edges may be substantially centered over the collapsed basin portion 34, such as in alignment with an axis bisecting the basin portion. In some configurations, a tag, label, or tab is a fixed to the first edge 100 and/or the second edge 102. The respective labels may be co-linearly aligned when the two edges are brought into adjacent alignment and may provide grasping surfaces and/or markers that a user is intended to grasp when opening drape 30. The respective labels may be positioned so that a user's hands are positioned at the inner-most surface of the drape when grasping at the labels, which can help minimize the risk of the user touching non-sterile equipment when opening the drape.

Figure 22:
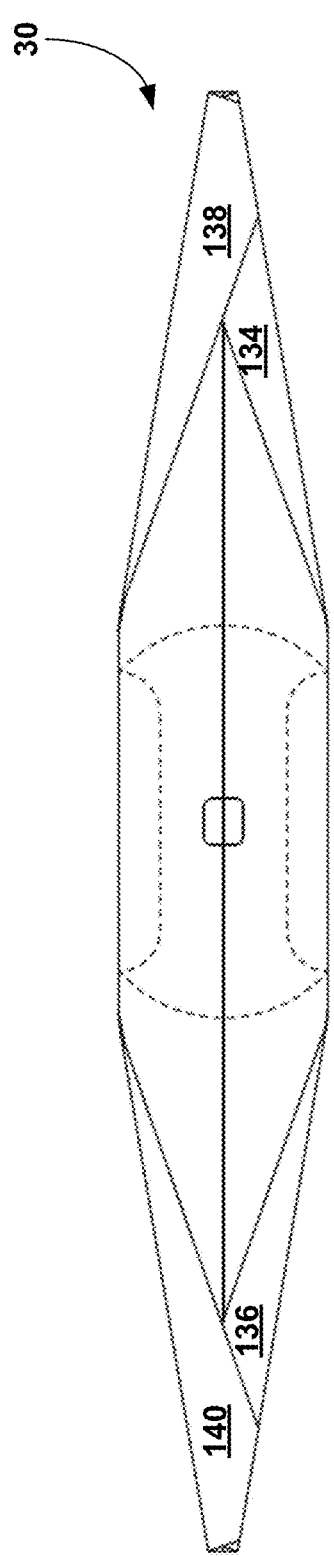

In some examples, drape 30 may be folded further beyond the vertically stacked arrangement illustrated in FIG. 19. For example, FIGS. 20-22 illustrate additional example folds that may be made to drape 30 to provide a compact folded drape structure. As illustrated in the example configuration of FIG. 20, for instance, opposed folded edges of drape 30 may be folded toward each other to reduce the overall size profile of the folded drape. For example, drape 30 may include a third perimeter edge 130 substantially perpendicular to the first edge 100 and the second edge 102. The drape may also include a fourth perimeter edge 132 on an opposite side of the drape from the third edge 130. Drape 30 may be folded by folding a corner 134 formed by an intersection of the third edge 130 with the first fold line 104 toward the second edge 102 and/or fourth fold line 120. It should be appreciated that the designation of a particular fold line number is used for purposes of discussion, and the fold line need not be in any particular numeric sequence or representative of any particular number of folds imparted to the drape. Drape 30 may also be folded by folding a corner 136 formed by an intersection of the fourth edge 132 with the first fold line 104 toward second edge 102 and/or fourth fold line 120.

Figure 24:
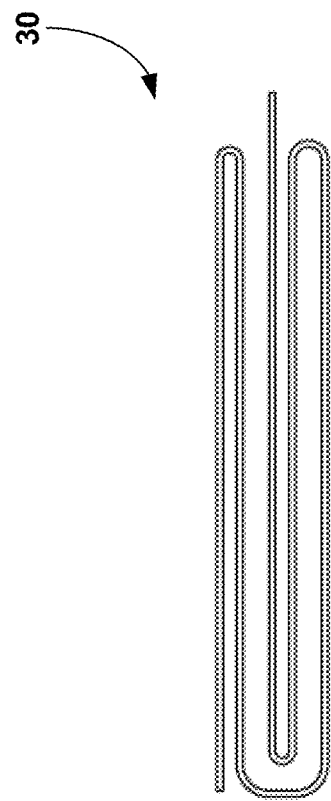
Figure 23:
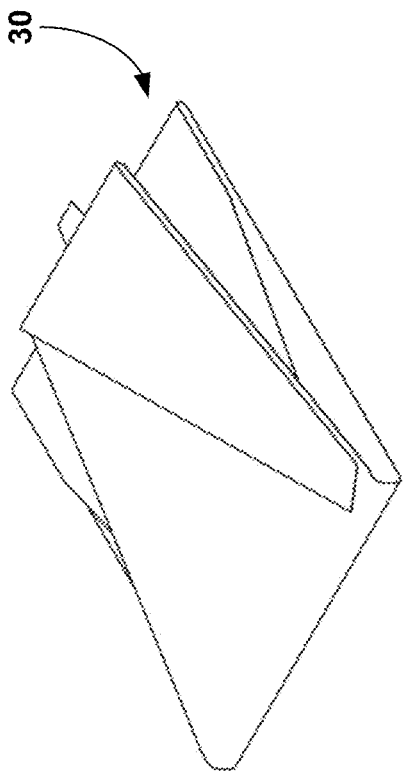

As shown in FIG. 21, a corner 138 formed by the intersection of the third edge 130 with the fourth fold line 120 may be folded toward first edge 100 and/or first fold line 104, overlapping corner 134. Additionally, a corner 140 formed by the intersection of the fourth edge 132 with the fourth fold line 120 may be folded toward the first edge 100 and/or first fold line 104, overlapping corner 136. The overlapping regions of corners 138 and 140 extending beyond the folded body of drape 30 may be tucked back under the folded body, as shown in FIG. 22. The ends of the resulting folded body may be folded, for example perpendicular to the basin portion 36, to define a resulting folded drape as illustrated in FIGS. 23 and 24.

Figure 25:
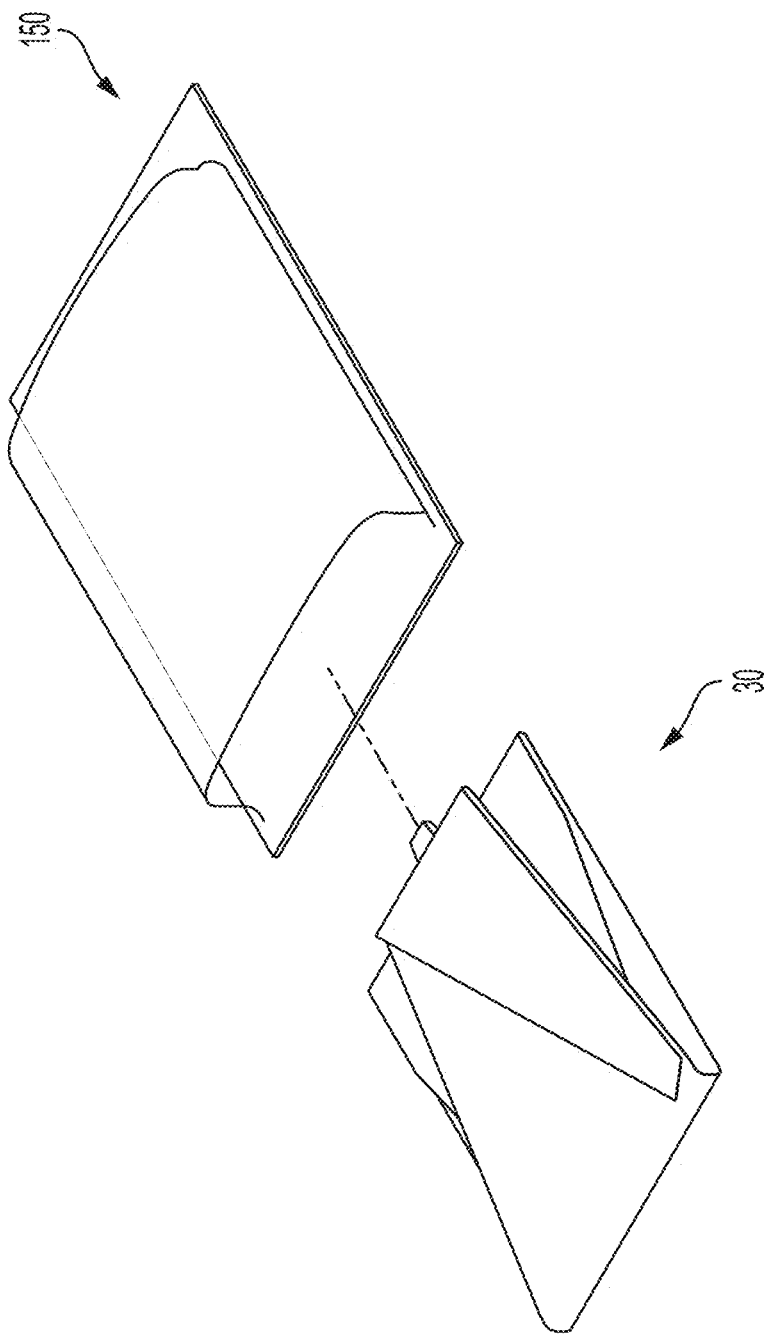

After folding, the folded drape may be inserted into a container 150, as shown in FIG. 25. Drape 30 and/or container 150 may then be subject to a sterilization treatment to sterilize drape 30 and/or the contents of container 150. Container 150 may be sealed (e.g., hermetically) to close drape 30 in the container before or after sterilization. In some examples, container 150 is formed of a polymeric material.

Figure 26:
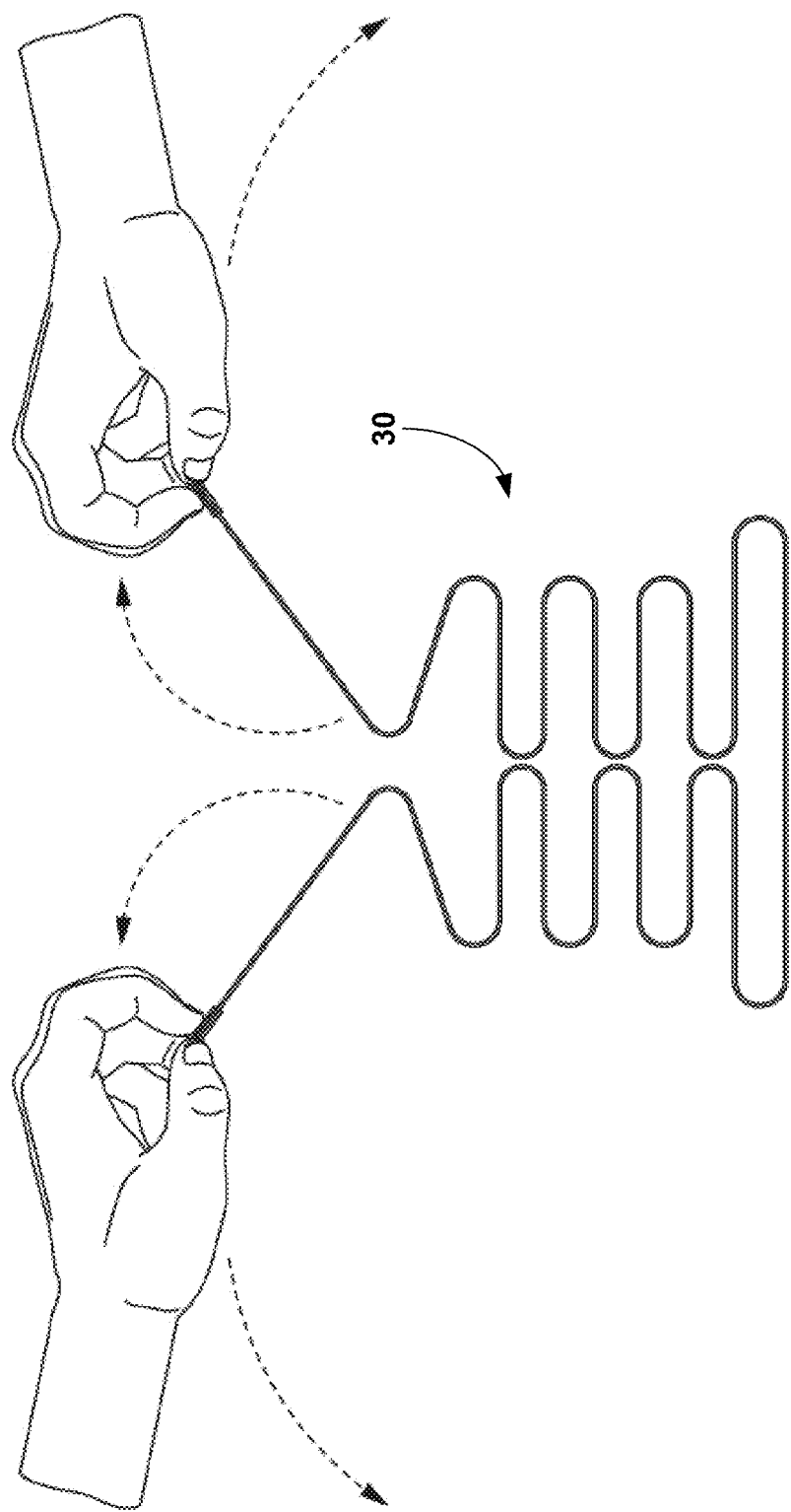

In use, an operator may open container 150 and remove drape 30 from the container. The operator may unfold the ends of the folded drape, e.g., reversing the folding process described above. The operator may place drape 30 and, more particularly, basin portion 36 of the drape over a corresponding basin of the equipment to be draped before fully unfolding the drape. For example, before the operator unfurls the vertically stacked folds imparted to drape 30, the operator may place the basin portion of the drape in/or over the basin of the equipment being draped. The operator may grasp first edge 100 and second edge 102, e.g., by grasping respective tabs or labels placed on each edge. The operator may then pull the edges outwardly and away from each other, unfolding the vertically folded drape sections, e.g., as illustrated in FIG. 26. In some examples, the operator may push the collapsed basin portion 36 downwardly into the basin of the equipment being draped, thereby expanding the collapsed basin portion of the drape and causing the basin portion to conform to the walls of the basin of equipment being draped. In either case, by folding drape 30 so that an operator can deploy the drape while minimizing the extent to which the outward facing surface of the drape is contacted during deployment, the likelihood that the sterile surfaces the drape may be contaminated during deployment are reduced.

Various examples have been described. These and other examples are within the scope of the following claims.

The invention claimed is:

1. A drape comprising:
   a thermoformed basin that is shape-indexed to a shape of a basin of a surgical system into which the thermoformed basin is configured to be inserted, the thermoformed basin being collapsible;
   a flexible side sheet bonded to and extending about an entire perimeter of the thermoformed basin, wherein a perimeter of the thermoformed basin has a length and a width; and
   at least one flexible window sheet positioned between and connected to the thermoformed basin and the flexible side sheet, the at least one flexible window sheet comprising a first flexible window and a second flexible window,
   wherein the at least one flexible window sheet is thermally bonded to both the thermoformed basin and the flexible side sheet,
   the first flexible window projects away from one lengthwise perimeter section of the thermoformed basin and is thermally bonded thereto,
   the second flexible window projects away from an opposite lengthwise perimeter section of the thermoformed basin and is thermally bonded thereto, and
   the flexible side sheet is thermally bonded to the thermoformed basin, the first flexible window, and the second flexible window about a perimeter defined, collectively, by the thermoformed basin, the first flexible window, and the second flexible window.

2. The drape of claim 1, wherein the thermoformed basin is collapsible from a height greater than 75 mm when expanded for use to a height less than 25 mm when collapsed for packaging.

3. The drape of claim 1, wherein the thermoformed basin defines a bottom wall and a sidewall extending upwardly and outwardly from the bottom wall of the thermoformed basin such that the thermoformed basin defines an open top surface of greater cross-sectional area than a cross-sectional area of the bottom wall.

4. The drape of claim 1, wherein the flexible side sheet extends at least 35 centimeters from the perimeter of the thermoformed basin about the entire perimeter of the thermoformed basin.

5. The drape of claim 1, wherein the thermoformed basin is formed of a polymer having a melt temperature greater than 130 degrees Fahrenheit.

6. The drape claim 1, wherein:
   the thermoformed basin is fabricated from a first polymer composition,
   the at least one flexible window sheet is fabricated from a second polymer composition different than the first polymer composition, and
   the flexible side sheet is fabricated from a third polymer composition different than the first polymer composition and the second polymer composition.

7. The drape of claim 6, wherein the first polymer composition, the second polymer composition, and the third polymer composition each comprise polyurethane.

8. The drape of claim 6, wherein the second polymer composition comprises a tackifying agent and the at least one flexible window sheet exhibits a coefficient of friction according to ASTM D1894 greater than 1.

9. The drape of claim 1, wherein the thermoformed basin has a thickness greater than a thickness of the flexible side sheet.

10. The drape of claim 1, wherein
    the thermoformed basin defines a bottom wall and a sidewall extending upwardly from the bottom wall of the thermoformed basin, the flexible side sheet being bonded to a perimeter edge of the sidewall, and
    the sidewall defines a thickness that increases from the perimeter edge of the sidewall to the bottom wall.

11. The drape of claim 10, wherein the thickness of the sidewall varies from a minimum thickness between 0.1 mm to 0.2 mm to a maximum thickness greater than or equal to 0.4 mm.

12. The drape of claim 11, wherein the maximum thickness ranges from 0.4 mm to 0.7 mm, and the flexible side sheet has a thickness ranging from 0.025 mm to 0.15 mm.

13. The drape of claim 1, further comprising an electronically readable tag, wherein:
    the electronically readable tag is a near field communication tag, and
    the near field communication tag is sandwiched between at least two sheets of material bonded together to define the at least one flexible window sheet.

* * * * *

UNITED STATES PATENT AND TRADEMARK OFFICE
CERTIFICATE OF CORRECTION

PATENT NO. : 11,730,555 B2
APPLICATION NO. : 16/144706
DATED : August 22, 2023
INVENTOR(S) : Heidi Frances Hendrix et al.

It is certified that error appears in the above-identified patent and that said Letters Patent is hereby corrected as shown below:

In the Claims

Column 18, Line 8, after "drape" insert -- of --

Signed and Sealed this
First Day of October, 2024

*Katherine Kelly Vidal*

Katherine Kelly Vidal
*Director of the United States Patent and Trademark Office*